United States Patent
Philips

(10) Patent No.: US 6,432,403 B1
(45) Date of Patent: Aug. 13, 2002

(54) ANTIBODIES TO POLYPEPTIDES HAVING PRENYLCYSTEINE CARBOXYL METHLYTRANSFERASE ACTIVITY OR INHIBITING ACTIVITY

(75) Inventor: Mark R. Philips, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/708,015

(22) Filed: Nov. 8, 2000

Related U.S. Application Data

(62) Division of application No. 09/095,758, filed on Jun. 11, 1998, now Pat. No. 6,184,016.
(60) Provisional application No. 60/049,304, filed on Jun. 11, 1997.

(51) Int. Cl.$^7$ .......................... A61K 39/00; C12P 21/08; C07K 16/00; C07K 16/40
(52) U.S. Cl. ............... 424/134.1; 530/387.3; 530/388.26; 530/389.1; 530/391.1; 530/391.3; 530/391.7
(58) Field of Search .................. 530/387.3, 388.26, 530/389.7; 424/134.1

(56) References Cited

U.S. PATENT DOCUMENTS

| | | |
|---|---|---|
| 5,043,268 A | 8/1991 | Stock |
| 5,202,456 A | 4/1993 | Rando |

FOREIGN PATENT DOCUMENTS

| | | |
|---|---|---|
| WO | 94/23025 | 10/1994 |
| WO | 98/13513 | 4/1998 |
| WO | 99/44878 | 4/1999 |

OTHER PUBLICATIONS

Kuby et al., 1994, Immunology, second edition, pp. 85–96.*
Glimcher et al, Fine specificity of cloned insulin–specific T cell hybridomas: evidence supporting a role for tertiary conformation, Dec. 1983, J. Immunology 131(6): 2868–74.*
Colman et al, Effects of amino acid sequence changes on antibody–antigen interaction, 1994, A structural view of immune recognition by antibodies, pp. 33–36.*
Ashby et al, "Isolation and DNA sequence of the STE 14 gene encoding farnesyl cysteine: carboxyl methyltransferase", *Yeast* 9(8):907–913 (1993).
Bovin et al, "Functional size of C–terminal protein carboxyl methyltransferase from kidney basolateral plasma membranes" *Biomchim Biophys Acta* 1207:114–119 (1994).
Boyartchuk et al, "Modulation of Ras and a–factor function by carboxyl–terminal proteolysis" *Science* 275(5307):1796–1800 (1997).
Dai et al, "Mammalian Prenylcysteine Carboxyl Methyltransferase Is in the Endoplasmic Reticulum", *J Biol Chem* 273(24):15030–15034 (1998).

Gibbs et al, "Farnesyltransferase inhibitors and anti–Ras therapy", *Breast Cancer Res and Treatment* 38(1):75–83 (1996).
Hrycyna et al, "Farnesyl cysteine C–terminal methyltransferase activity is dependent upon the STE14 gene product in *Saccharomyces cerevisiae*", *Mol Cell Biol* 10(10):5071–5076 (1990).
Hrycyna et al, "The *Saccharomyces cerevisiae* STE14 gene encodes a methyltransferase that mediates C–terminal methylation of a–factor and RAS proteins", *EMBO J* 10(7):1699–1709 (1991).
Imai et al, "Genes encoding farnesyl cysteine carboxyl methyltransferase in Schizosaccharomyces pombe and *Xenopus laevis*", *Mol Cell Biol* 17(3):1543–1551 (1997).
Koblan et al, "Farnesyltransferase inhibitors: a new class of cancer chemotherapeutics", *Biochem Soc Trans* 24:1993–1997 (1996).
Marshal, "Protein Prenylation: A Mediator of Protein–Protein Interactions", *Science* 259:1865–1866 (1993).
Oliff et al, "New Molecular Targets for Cancer Therapy", *Sci Am* 275(3):144–149 (1996).
Park et al, "Crystal Structure of Protein Farnesyltransferase at 2.25 Angstrom Resolution", *Science* 275:1800–1804 (1997).
Philips et al, "Carboxyl Methylation of Ras–Related Proteins During Signal Transduction in Neutrophils", *Science* 259(5097):977–980 (1993).
Philips et al, "Activation–dependent carboxyl methylation of neutrophil G–protein gamma subunit", *Proc Natl Acad Sci USA* 92)6_;2283–2287 (1995).
Philips et al, "Prenylcysteine–Directed Carboxyl Methltransferase Activity in Human Neutrophil Membranes", *Methods Enzym* 256:49–63 (1995).
Pillinger et al, "Characterization of a Plasma Membrane–associated Prenylcysteine–directed alpha Carboxyl Methyltransferase in Human Neutrophils", *J Biol Chem* 269(2):1486–1492 (1994).
Sapperstein et al, "Nucleotide Sequence of the Yeast STE14 Gene, which Encodes Farnesylcysteine Carboxyl Methyltransferase, and Demonstration of its Essential Role in a–Factor Export", *Mol Cell Biol* 14(2):1438–1449 (1994).
Volker et al, "Prenylcsysteine Analogs to Study Function of Carboxylmethylation in Signal Transduction", *Methods in Enzym* 250:216–224 (1995).
Database EMBL Emest 16, Entry MMAA22288; Accession No. AA022288; Nov. 29, 1996.
Database EMBL Emest, Entry HSAA43108; Accession No. AA143108; Dec. 14, 1996.

* cited by examiner

*Primary Examiner*—Christina Y. Chan
*Assistant Examiner*—Phuong Huynh
(74) *Attorney, Agent, or Firm*—Browdy & Neimark, P.L.L.C.

(57) ABSTRACT

An antibody specific for the mammalian protein prenylcysteine carboxyl methyltransferase.

7 Claims, 10 Drawing Sheets

FIG. 2

```
Human pcCMT       --------------MAGCAARAPPGSEARLSLATFLLGASVLAL.PLLTR.........AGLQGRTGLAL  46
Mouse EST         PGYSRRFGPLVRRLFRRPAHGGCAARFRGLRGAPQPRYIPPGRLGARSAAAHARRPAGRTALAL  65
X. laevis mam4    -------------MAGARLLQEGRVEIVSFTLGASVISL..PLLTSSFTEQTLLAAAPGRIALVF  50
C. elegans Cos1   -------------MPPIPPPTFVGRIAFHLKSDDDFRTAIDAFMASFAVVATVSASTSSFVFGILASL  55
C. elegans Cos 2  -------------MAPNSTPPPTFFGRIVFHLTSDDVFRTAIFAFIASFTVIAAVASVTGSFLVGLLASV  57
S. cerevisiae Ste14 ---------------------------------------------------------MHQD  4
S. pombe mam4     ----------------------------------------------------------------

Human pcCMT       YVAGLNALLLLLYRPPRYQIAIRACFLGFVFGCGTLLSFSQSS..WSHFGWYMCSLSLFHYSEYL  109
Mouse EST         YVAGLNALLLLLYRPPRYQIAIRACFLGFVFGCGVLLSFSQSS..WNHFGWYVCSLSLFHYSEYL  128
X. laevis mam4    FIAALNGLLLLLLYKAQLYQVAIRASFLGFAFGCGLLLSITQSP..WKPFGWYVCSLSFFHYSEYL  113
C. elegans Cos1   LTILIAYLFARKRVFTNKSILMPAALLGCAVAVSLAYSVSHEGEVLEHLSHYFLFLSMFHFTEFV  120
C. elegans Cos 2  IVLLVAYAVGESCEFINNQILMPAAFLGCAVAVNLVYTVAHEGELWEYFSRYFLFLSVFHFSEFV  122
S. cerevisiae Ste14 FQEDEHEYPDIRRN.PLHEVTMTSYILGILLGIFVGLFP..QIRF.XNFNLFIIALSLFHFLEYY  65
S. pombe mam4     ------MGNLHTSIAVASICLTSAFLGCVFGL..GFFV..WIIYGYSIGGFFAFLSLFHFLEFY  54

Human pcCMT       VTAVNNPKSLSLDSFLLNHSLEYTVAALSSWLEFTLENI....FWPELKQITWL........SV  161
Mouse EST         VTAVNNPKSLSLDSFLLNHSLEYTVAALSSWIEFTLENI....FWPELK---------------  173
X. laevis mam4    VTAMNNPRSLSIDSFLLNHSLEYTLAALSSWVEFTIETT.....IYPDLKQITWL........SV  165
C. elegans Cos1   FTALTNRRTLRPDSFLLNHSVGYWLAASISWIEFLIE......AYFFPEIKMRGILW.......  171
C. elegans Cos 2  FTALTNRRTLGPDSFLLKHSFGYWLAASIGWIEFLIE......ANFYPEIKMYSVLW.......  173
S. cerevisiae Ste14 ITAKYNPLKVHSESFLLNNGKSYMAAHSFAILECLV..ESF.LFPDLKI..FSYSLATKLCTV  123
S. pombe mam4     ITARFQGSQLSWDSFILNNGKAYWLAMLVGLLECLLSGGKSFAKVINCLRFPSFLINFIFSVYQT  119

Human pcCMT       TGLLMVVFGECLRKAAMFTAGSNFNHVVQNEKSDTHTLVTSGVYAWFRHPSYVGWFYWSIGTQVM  226
Mouse EST         IGLIMVLFGEVLRKCAMLTAGSNFNHIVQNEKSDSHTLVTSGVYSWFRHPSYVGWFYWSIGTQVL  230
X. laevis mam4    VTAMNNPRSLSIDSFLLNHSLEYTLAALSSWVEFTIETT    -- IGTLGCIIGEIFRKVGMVHAGLAFTHRLAMTKRSDHRLVKDGIYAYLRHPGYFGWFLWAVSTQII  236
C. elegans Cos1   IGTFGCIIGEIVRKVGMVHAGLAFTHLMARTKRSGHTLINTGIYAYMRHPGYFGWFIWAVSTQIV  238
C. elegans Cos 2  LGCLLVILGQYTRTIAMHTAGHSFSHIVKTKKESDHVLVKTGVYSWSRHPSYLGFFWWAIGTQLL  188
S. cerevisiae Ste14 ITARFQGSQLSWDSFILNNGKAYWLAMLVGLLECLLSGGKSFAKVINCLRFPSFLINFIFSVYQT SALGFLCLGQYLRSSAMVQAGQSFSHIVASKRNKDHLLVTDGIYAYVRHPSYVGFFIWALGTQML  184

Human pcCMT       LCNPICGVSYALTVWRFFRDRTEEEEISLIHFFGEEYLEYKKKRVPTGLPFFIKGVKVDL  284
X. laevis mam4    LCNPLCLVGDTVASWRFFSERIEEEEFSLIHFFGENYLEYKKKVPTGLPFFIKGVKMEP  288
C. elegans Cos 1  LCNPICCVVYAYVTWHFFASRIYDEEKDLISFFGDSYVEYQQNVWCGVPFVRGYQRP-   293
C. elegans Cos 2  LCNPISFVIYTFVTWRFFANRIEIEEKDLISFFGDDYAEYQRKTWSGVPFARGYQKP-   295
S. cerevisiae Ste14 LLNPLSLVIFIFVLWKFFSDRIRVEEKYLIEFFSAEYIEYKNKVGVGIPFI------   239
S. pombe mam4     LGNFVSTLLFSLVLWKFFSQRITTEEAYLVSFFGDSYEQYRKKVPSGIPLIP------  236
```

ANTIBODIES TO POLYPEPTIDES HAVING PRENYLCYSTEINE CARBOXYL METHLYTRANSFERASE ACTIVITY OR INHIBITING ACTIVITY

CROSS-REFERENCE TO RELATED APPLICATIONS

This is a division of parent application No. 09/095,758 filed Jun. 11, 1998, now U.S. Pat. No. 6,184,016, which claims priority of U.S. provisional application No. 60/049,304, filed Jun. 11, 1997.

GOVERNMENT LICENSE RIGHTS

The U.S. Government has a paid-up license in this invention and the right in limited circumstances to require the patent owner to license others on reasonable terms as provided for by the terms of Grant Nos. Al36224 and GM55279 awarded by the National Institute of Health.

BACKGROUND OF THE INVENTION

1. Field of the Invention

The present invention relates to the field of post-translational modification of proteins, and more particularly, to an enzyme catalyzing carboxyl methylation of signaling molecules and DNA encoding same. The present invention also relates to a method of screening for inhibitors of carboxyl methylation, which inhibitors may serve as therapeutic agents in the treatment of inflammation and cancer.

2. Description of the Related Art

Proteins that are post-translationally modified by prenylation (farnesylation or geranylgeranylation) of a C-terminal cysteine are usually further modified by proteolysis and α-carboxyl methylation. There are two major classes of proteins that are prenylated on cysteine residues. The first major class of these prenylated proteins are those which end with the sequence CysXaaXaaXaa (SEQ ID NO:6), hereinafter referred to as CXXX, indicating that the primary translation product has a cysteine four residues from the C-terminus. Proteins of this class are often referred to as CAAX proteins, where A=aliphatic amino acid and X=any amino acid, because most, but not all, such proteins have aliphatic residues at the indicated positions (Clarke, S., 1992).

Among the large number of proteins ending with the CXXX consensus signal for prenylation are yeast mating pheromones, nuclear lamins, members of ras and Rho families of the Ras superfamily of GTPases, and the γ subunits of heterotrimeric guanine nucleotide-binding regulatory (G) proteins.

In most cases, the final amino acid of the CXXX sequence determines whether the primary translation product is farnesylated or geranylgeranylated on the C-terminal cysteine residue by two related (type I) but distinct prenyltransferases. If the final amino acid of the C-terminus is leucine or phenylalanine, the primary translation product is geranylgeranylated (Finegold et al, 1991; Kinsella et al, 1992). Other amino acids, such as serine, methionine, or glutamine, at the final amino acid position, causes the primary translation product to be farnesylated. Thus, cytosolic type I prenyltransferases recognize the CXXX consensus sequence and catalyze the attachment of a 15-carbon farnesyl or 20-carbon geranylgeranyl polyisoprene chain via a thioether linkage to the cysteine residue (Glomset et al, 1990; Maltese, W. A., 1990; Seabra et al, 1991).

Once prenylated, these proteins become substrates for a protease that removes the XXX sequence (final three amino acids at the C-terminus), leaving the prenylcysteine as the new C-terminus. It is this C-terminal prenylcysteine moiety that then becomes a substrate for prenylcysteine carboxyl methyltransferase, which methylesterifies the α carboxyl group (Clarke et al, 1988; Stephenson et al, 1990). Unlike prenylation and proteolysis, however, carboxyl methylation is reversible under physiologic conditions (Venkatasubramanian et al, 1980; Chelsky et al, 1985). FIG. 1 schematically illustrates the series of post-translational modifications of proteins having the C-terminal CXXX consensus sequence using a Rho-protein as an example.

The other major class of prenylated proteins is the rab family of ras-related GTPases which end with the sequence CysXaaCys or CysCys. One or both of the C-terminal cysteine residues are geranylgeranylated by a distinct type II geranylgeranyl transferase. The C-terminal geranylgeranylated cysteine residues of rab proteins are also substrates for prenylcysteine carboxyl methyltransferase.

Yeast mating pheromones absolutely require carboxyl methylation for their interaction with receptors. The gene product of the wild-type Ste14 gene characterized and sequenced in *Saccharomyces cerevisiae* was identified to be the farnesylcysteine C-terminal carboxyl methyltransferase which mediates the C-terminal methylation of the yeast a-factor pheromone and the ras proteins of *S. cerevisiae* (Hrycyna et al, 1990 and 1991; Ashby et al, 1993). In human neutrophils, the laboratory of the present inventor reported that renylcysteine carboxyl methylation of Rho GTPases is stimulated by inflammatory agonists and that agents that block prenylcysteine carboxyl methyltransferase inhibit neutrophil signal transduction, (Philips et al, 1993). Thus, inhibitors of prenylcysteine carboxyl methyl transferase are expected to serve a therapeutic role as anti-inflammatory agents.

The family of Ras proteins which are prenylated play a central role in the regulation of cell growth and integration of the regulatory signals which govern the cell cycle and proliferation. It is now known that there are four alleles of ras, H-ras, K-ras (both exon 4a and 4b splice variants), and N-ras, in mammalian cells. Mutants of these ras genes were among the first oncogenes to be identified for their ability to transform cells to a cancerous phenotype (Barbacid, 1987), and mutations of the ras genes (H-ras, K-ras, and N-ras) have been demonstrated to be associated with unregulated cell proliferation and are found in an estimated 30% of all human cancers (Rodenhuis, 1992).

The function of normal and oncogenic Ras proteins is absolutely dependent on the series of post-translational modifications (see FIG. 1). Indeed, such post-translational modifications are necessary for both membrane targeting and localization. Because Ras function is dependent on the localization to the plasma membrane and association with the plasma membrane, and because constitutively active mutant Ras proteins and several other prenylated Ras-related GTPases have the capacity to transform cells, it has been recognized that each of the enzymatic post-translational modification steps are new drug targets (Gibbs, 1991). There has been much activity in developing inhibitors of prenyltransferases, which catalyze the first step of the post-translational modifications, to block the membrane targeting and localization of the Ras protein (Koblan et al, 1996). Tests have shown that prenyltransferase inhibitors block the maturation of the Ras protein and reverse the cancerous transformation induced by mutant ras genes in cell culture and that the formation of new tumors by abnormal Ras proteins was prevented in animals. Furthermore, the farnesyl transferase inhibitors appear to be quite specific and do not affect normal cells (Koblan et al, 1996; Gibbs et al, 1996; Oliff et al, 1996).

It is expected that inhibitors that target and block prenylcysteine carboxyl methyltransferase, the third step of the post-translational modification, will also serve as a therapeutic in cancer treatment as well as in other hyperproliferative disorders, such as psoriasis, precancer, etc. Prenylcysteine carboxyl methyltransferases, however, have defied biochemical purification because they cannot be extracted from biological membranes in an active state. Thus, no tool useful in identifying such inhibitors has existed in the prior art.

Citation of any document herein is not intended as an admission that such document is pertinent prior art, or considered material to the patentability of any claim of the resent application. Any statement as to content or a date of any document is based on the information available to the applicant at the time of filing and does not constitute an admission as to the correctness of such a statement.

SUMMARY OF THE INVENTION

The present invention relates to mammalian prenylcysteine carboxyl methyltransferase (pcCMT), and particularly to a human pcCMT that is the first mammalian pcCMT to be isolated away from human cells and other human proteins in active form and to specific antibodies thereto. The present invention also relates to a recombinant DNA molecule which includes a nucleotide sequence encoding human prenylcysteine carboxyl methyltransferase, as well as an expression vector thereof, and a host cell transformed with the expression vector. The present invention further relates to methods of screening for inhibitors of mammalian prenylcysteine carboxyl methyltransferase activity, which inhibitors are expected to serve as therapeutics in the treatment of inflammation and hyperproliferative disorders such as cancer.

BRIEF DESCRIPTION OF THE DRAWINGS

FIG. 2 shows an amino acid sequence alignment between the deduced amino acid sequence of human pcCMT (SEQ ID NO:5) and the related genes and sequences of mouse expressed sequence tag (EST) mh77d06.r1 (SEQ ID NO:7), Xenopus laevis mam4 (SEQ ID NO:8; Imai et al, 1997), two C. elegans genes identified by search of the NCBI GenBank database, S. cerevisiae Ste14 (SEQ ID NO:11; Ashby et al, 1993) and S. pombe mam4 (SEQ ID NO:12; Imai et al, 1997). Amino acid identities between human pcCMT and the other gene products are indicated by dark shading. Hydrophobic stretches of human pcCMT that may represent membrane-spanning domains are indicated with solid bars and a region of 36% identity between human pcCMT (amino acid residues 1–66 of SEQ ID NO:5) and the amino acids 750–821 of human band 3 anion transporter is indicated with a dashed bar. An internal peptide used to raise an anti-pcCMT antiserum is indicated by a dotted line. A potential N-glycosylation site is indicated with an arrowhead.

FIG. 4A shows hydrophilicity.

In FIG. 5A, neutrophil cytosol (CS) containing a mixture of Rho family proteins complexed with Rho-GDI (lanes 2, 3, 6, 7, 10, 11) or RhoA-GDI complexes partially purified from CS (lanes 4, 8, 12) were incubated with the methyl donor S-adenosyl-L-[methyl-$^3$H] methionine and light membranes derived from nitrogen cavitation of human neutrophils (lanes 1–4) or COS-1 cells transiently transfected with either human pcCMT (lanes 5–8) or vector alone (lanes 9–12). In some reactions (lanes 3, 7, 11) a competitive pcCMT inhibitor, AFC, was included. Reaction products were analyzed by SDS-PAGE and fluorography. The position of carboxyl methylated p21s is indicated as is the position of protein phosphatase 2a (PP2a) that is methylated on a C-terminal leucine by an enzyme unrelated to pcCMT (Lee et al, 1993). In FIG. 5B, the analysis as done in FIG. 5A shows GTP-dependence (10 μM GTPγ5) of carboxyl methylation of partially purified human neutrophil Rac2 and RhoA, but not cdc42hs, by COS-1 cell membranes expressing human pcCMT.

In FIG. 6A polyadenylated mRNA was prepared from HL60 cells that had been grown in DMEM +10% fetal calf serum without (lane 1) or with (lane 2) 5% DMSO for five days to induce granulocytic differentiation. Membranes were probed with [$^{32}$P]-labeled full-length pcCMT cDNA (upper panel) and later stripped and reprobed for β-actin mRNA (lower panel). The results shown are representative of two independent experiments. In FIG. 6B, a membrane containing polyadenylated mRNA from the indicated human tissues was modified as in FIG. 6A for pcCMT RNA (upper panel) and subsequently β-actin mRNA (lower panel) according to the manufacturers' instructions (Clontech, Palo Alto, Calif.). In FIG. 6C, lysates of HL60 cells metabolically labeled with [$^{35}$S] methionine/cysteine were immunoprecipitated (lanes 2 and 3) with preimmune (p) or immune (i) serum from rabbit immunized with a pcCMT peptide. Membranes from human neutrophils (PMN) and from COS-1 cells transfected with pcCMT (CMT) or vector alone (VEC) were immunoblotted with the same sera (lanes 4 and 5).

In FIGS. 7A–7E, CHO cells (FIGS. 7A–7C) and COS-1 cells (FIGS. 7D and 7E) were transiently transfected with GFP alone (FIG. 7A) or GFP-tagged human pcCMT (FIGS. 7B–7E) and examined unfixed. In FIGS. 7C and 7E, the image is intentionally overexposed to reveal the distinct fluorescence of the ER and absence of plasma membrane fluorescence. Arrowheads indicate nuclear envelope fluorescence and asterisks indicate a perinuclear area of intense Golgi fluorescence. In FIG. 7F, CHO cells transfected with GFP-tagged pcCMT were fixed, permeablized, and stained for the ER marker ribophorin I (Texas-Red) and viewed by confocal microscopy (0.4 μM optical section) where yellow pseudocolor indicates overlap. In FIG. 7G, CHO cells transfected with Myc-tagged human pcCMT were fixed, permeablized, and stained with anti-Myc antibody 9E10 (Texas-Red). In FIGS. 7H and 7I, untransfected COS-1 cells were stained for endogenous pcCMT with preimmune serum (FIG. 7H) or immune anti-peptide antintiserum (FIG. 7I). Bars indicate 10 μM.

In FIG. 8A, COS-1 cells were transiently transfected with GFP-Nras and observed live at 24 hours by epifluorescence microscopy to reveal both surface membrane (arrowheads) and intense perinuclear (Golgi) fluorescence. The position of the nuclease is marked (N). FIG. 8B shows the cytosolic localization of GFP-NrasC186S, a mutant defective in prenylation. FIG. 8C shows the predominantly cytosolic localization of GFP-Nras in cells exposed to 200 µM AFC during the 24-hour transfection. Bars indicate 10 µM.

DETAILED DESCRIPTION OF THE INVENTION

Figure 1:
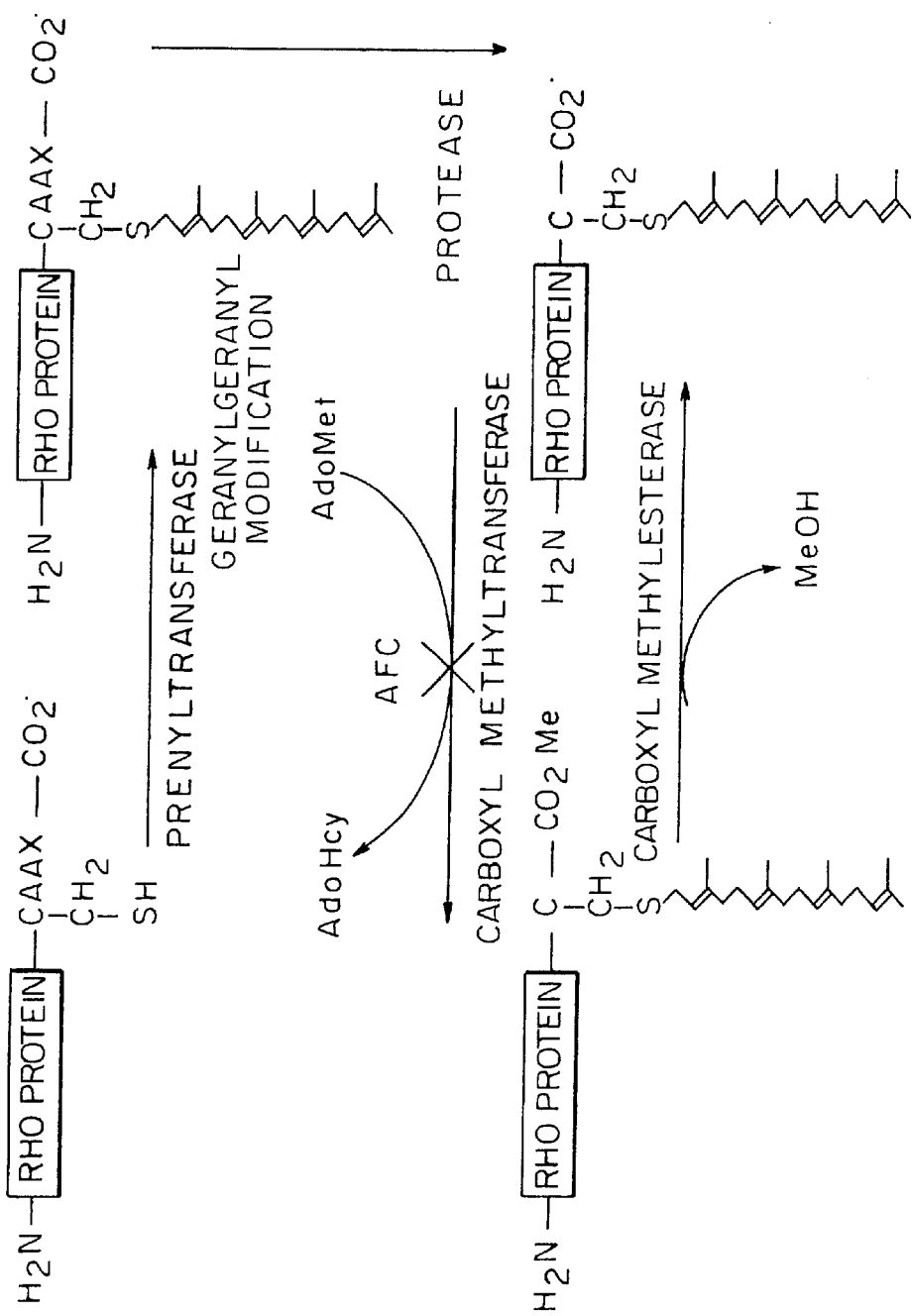
FIG. 1 schematically illustrates the post-translational processing of a Rho-family Ras-related protein.
Figure 3:
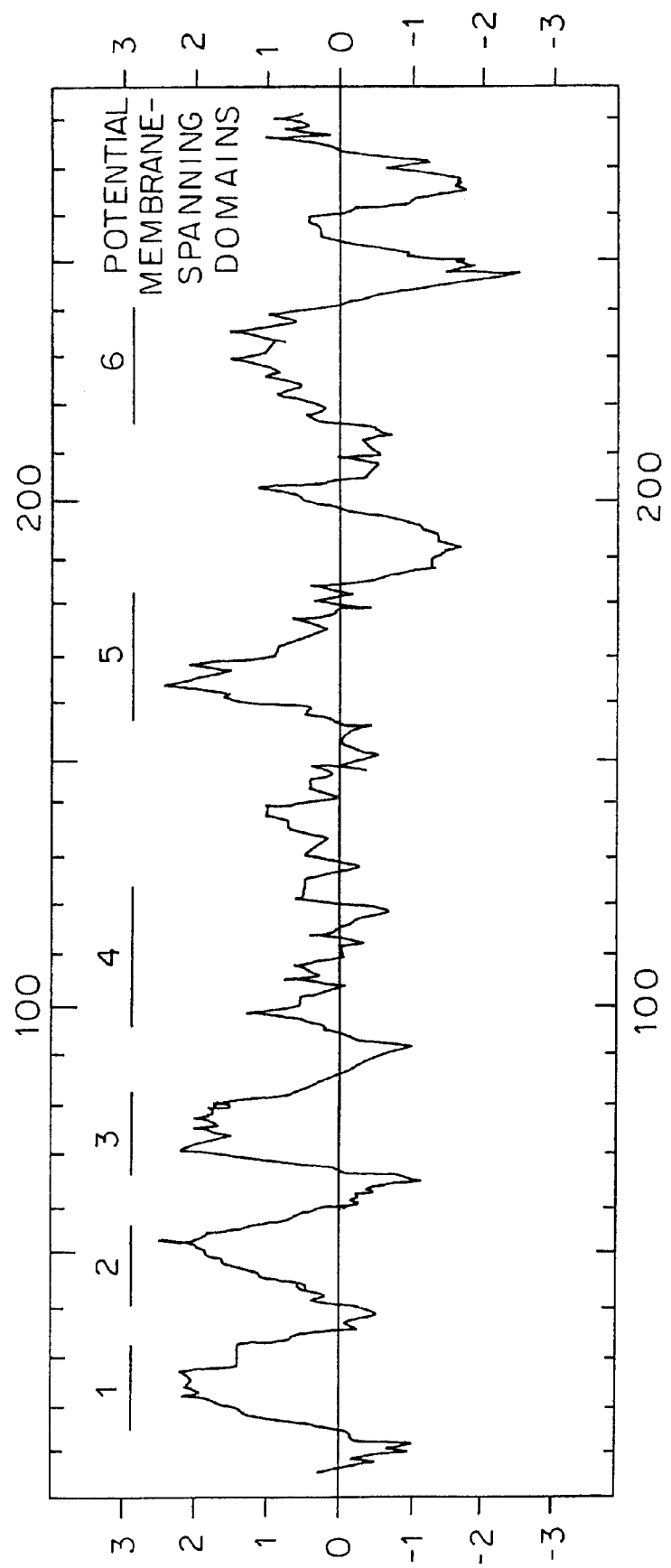
FIG. 3 shows a Kyte-Doolittle hydrophobicity plot of human pcCMT.

A gene expressed in human myeloid cells which encodes a prenylcysteine carboxyl methyltransferase (pcCMT) has been identified and characterized, and is the first such gene to be isolated from a mammal. As shown in FIG. 2, the deduced 284 amino acid sequence (SEQ ID NO:5) of human pcCMT was found to have 31% identity (over amino acid residues 60–277) to a previously described pcCMT of $S.$ $cerevisae$, designated Ste14 (Ashby et al, 1993). However, the first 60 amino acid residues showed no similarity to the yeast gene product but was found to be homologous to the 11th and 12th membrane-spanning domains of a mammalian anion transporter, band 3. Hydropathy analysis, as shown in FIG. 3, revealed six membrane spanning domains, consistent with membrane localization and detergent lability of pcCMT activity.

Despite persistent attempts, prenylcysteine carboxyl methyltransferases have previously defied biochemical purification because pcCMT cannot be extracted from biological membranes in an active state. Before the human pcCMT according to the present invention was cloned and characterized as described in the Example herein, the only pcCMT characterized at the molecular level (by complementation of a mating-deficient mutant) was the $S. cerevisiae$ Ste14 gene product. Attempts to clone pcCMT from vertebrates by homology to Ste14 have failed. However, according to the present invention, a cDNA encoding human pcCMT was finally cloned and sequenced, and the protein was characterized from its deduced amino acid sequence. It was only after the present human pcCMT was cloned, sequenced and characterized by the laboratory of the present inventor that the cloning of a $Schizosaccharomyces$ $pombe$ mam4 gene and a $Xenopus$ $laevis$ mam4 gene by complementation and transcomplementation of $S.$ $pombe$ mam4 mutants, respectively, was independently reported (Imai et al, 1997). Even these sequences, however, do not render obvious the gene and protein sequences of the present invention.

In the context of the present invention, the term "prenylcysteine carboxyl methyltransferase", also referred to herein as "pcCMT", is intended to encompass any mammalian pcCMT and any naturally occurring variants thereof having at least 70% identity to the amino acid sequence of SEQ ID NO:5. The term is also intended to include muteins in which one or more amino acid residues of SEQ ID NO:5 has been substituted with a different amino acid, deleted, or added, provided that the amino acid sequence of the mutein has at least 70% identity to SEQ ID NO:5, such as at least 85% identity, at least 90% identity or at least 95% identity. To be a naturally occurring variant or mutein of the human pcCMT according to the present invention, it must have or substantially retain the same carboxyl methyltransferase activity of the human pcCMT of SEQ ID NO:5.

For the purpose of this specification and claims, unless otherwise stated, the percentage sequence identity between two sequences is to be determined by (1) aligning to maximize the local similarity score between the two sequences, and (2) expressing the number of identical aligned pairs as a percentage of (a) the total length of the overlap region, including nulls (gaps), or (b) the original of the shorter sequence, whichever of (a) or (b) is larger.

The two sequences are to be aligned by a rigorous (linear programming) based local alignment algorithm in which the overall similarity score for a given alignment is obtained by summing the pairwise alignment scores, for each aligned pair of amino acids, and a gap penalty for each gap introduced into either sequence in an attempt to improve the overall similarity score for the alignment. The pairwise alignment scores are derived from a 20×20 scoring matrix for amino acids. The gap penalties are a linear combination of a gap initiation penalty imposed for the first null of a given gap, and a gap extension penalty for each additional null added to that gap. Only internal gaps will be penalized. For amino acid sequence alignment, the scoring matrix will be the PAM250 matrix, in the form wherein the scores range from +17 to −8; the gap initiation penalty will be −12; and the gap extension penalty will be −4.

In addition, the term "isolated mammalian prenylcysteine carboxyl methyltransferase" is intended to encompass any mammalian pcCMT that is isolated away from its native cells, native cell fractions, and other native proteins. For instance, an "isolated mammalian prenylcysteine carboxyl methyltransferase" includes, but is not limited to, mammalian pcCMT expressed in non-native host cells, mammalian pcCMT obtained as part of a membrane preparation of non-native cells, mammalian pcCMT extracted from membranes of non-native cells, and mammalian pcCMT associated with phospholipid vesicles/liposomes. By the term "membrane", it is intended to not only encompass the various membranes of cells but any artificial membrane-like structures, such as for example phospholipid vesicles/liposomes.

Proteins may be modified by any art-recognized means, including:

(a) expression, in a suitable host cell, of a modified gene which encodes the modified protein;

(b) biosynthesis of a precursor protein in a host cell which post-translationally modifies the precursor protein (e.g., crosslinking of cysteines; glycosylation; hydroxylation of prolines; phosphorylation of tyrosines; lipidation of C-terminals; cleavage);

(c) biosynthesis of the protein in a host cell engineered to provide a tRNA charged with a modified amino acid;

(d) non-biological synthesis of the modified protein by stepwise addition of amino acids and/or peptide fragment condensation;

(e) chemical or enzymatic modification of a precursor protein, with or without use of a linker;

(f) fragmentation of a precursor protein and, optionally, linkage of one or more fragments to additional amino acids or peptides; and combinations thereof.

For the sake of convenience, modifications are divided into those achievable by (a) above, which will be termed "mutations", and those which are not, which will be termed "derivatizations."

While normally derivatives are prepared by first synthesizing the lead molecule and then derivatizing it, derivatives may also be prepared directly. However, implicit in the term "derivatives" is that it is technically feasible to obtain the derivative by modification of the lead molecule, even if that is not the preferred method of production.

Modifications of proteins may be classified as follows:

Favorable—these modifications enhance the utility of a protein for a particular use.

Neutral—these modifications neither enhance nor diminish the utility of a protein for a particular use.

Unfavorable—these modifications diminish, but do not necessarily eliminate, the utility of a protein for a particular use.

Inactivating—these modifications eliminate the utility of a protein for a particular use.

Tolerable—these modifications are favorable, neutral, or unfavorable, but not inactivating.

It is possible, since a protein may have more than one use, that a modification is favorable for one use, unfavorable for a second, neutral for a third, and inactivating for a fourth.

In general, we will discuss the effect of modifications on the suitability of the protein for uses which are specific, to a greater or lesser degree, on the specific structure of the protein, rather than on those which are dependent only on the protein's amino acid composition, molecular weight, or gross physical properties.

A protein may be modified for a variety of reasons, including one or more of the following purposes:

to render the molecule more detectable, as in the case of radiolabeled, enzyme labeled, and fluorescent labeled derivatives;

to render the molecule more stable with respect to a particular physical, chemical, or biological agent, such as heat, light, oxidizing agents, reducing agents, and enzymes;

to render the molecule more soluble in a solvent of interest, e.g., to facilitate its administration, or less soluble, e.g., to facilitate its precipitation or to allow its use in capturing another molecule;

to limit the nature of the reactions which the molecule can participate in, e.g., placing protective groups on amino acid side chains, or conversely, to expand the possible reactions, e.g., placing a reactive group on the molecule to facilitate a subsequent coupling reaction;

to render the molecule less (or more) immunogenic;

to increase (or decrease) the time which the molecule resides in a particular organ or tissue if administered to a subject, or to hasten (or slow) its arrival in a particular organ or tissue;

to enhance (or diminish) one or more of its biological or immunological activities, e.g., to increase or decrease its affinity for a receptor, or to alter its specificity; or to confer a new activity which complements a prior activity (e.g., attaching a toxin to an antitumor antibody); or to inhibit an undesirable side effect of the molecule.

Most residues of a protein can tolerate some degree of mutation. Mutations may take the form of single or multiple substitutions, insertions, or deletions. Preferably, insertions or deletions are directed to the termini of the molecule, or to surface loops or interdomain boundaries. Preferably, internal insertions and deletions are of no more than five residues, absent evidence (such as an example in a homologous protein) that a larger internal insertion or deletion could be tolerated.

There is no preferred maximum with respect to an insertion at a terminus, which is more aptly termed an "addition" or "fusion". It is routine to fuse one protein to another to facilitate expression, or to provide a fusion protein which has the combined biological activities of its components. A fusion protein may be useful as a precursor, which can be cleaved to liberate an active protein, even if the fusion protein itself lacks activity.

With regard to deletion at a terminus, more aptly termed "truncation", the purpose of the modification is important. It is routine to extensively truncate a protein when one is interested only in its immunological properties.

One may abstract from a protein an epitope as small as five amino acids, and use it by itself to elicit a T cell response, or conjugated to copies of itself or to an immunogenic carrier to elicit a B cell response. When it is a biological activity which must be preserved, the limits on truncation may be more stringent.

Preferably, after considering substitutions, and any internal deletions and insertions, the mutant is at least 85%, more preferably at least 90%, and most preferably at least 95%, identical in sequence to the original protein.

A protein is more likely to tolerate a mutation which (a) is a substitution rather than an insertion or deletion;

(b) an insertion or deletion at the termini, than internally, or, if internally, at a loop or an interdomain linker;

(c) affects a surface residue rather than an interior residue;

(d) affects a part of the molecule distal to the binding site;

(e) is a substitution of one amino acid for another of similar size, charge, and/or hydrophobicity; and (f) is at a site which is subject to substantial variation among a family of homologous proteins to which the protein of interest belongs.

These considerations can be used to design functional mutants.

Preferably, for the framework residues, and more preferably for the whole chain, the predicted or experimentally determined 3D structure of the modified protein has a main chain ($C^\alpha$-carbon) conformation whose root-mean-square deviation from the predicted or experimentally determined 3D structure of the original protein is preferably less than 5Å, more preferably less than 3 Å, still more preferably less than 2 Å, most preferably less than 1 Å.

The most accurate method for the prediction of a protein structure is model building from a protein or proteins of known structure that have been identified as homologous from sequence analysis. Surprisingly, proteins with very little detectable sequence identity can still fold into very similar structures.

The coordinates of protein structures can be obtained from Protein Data Bank or the Cambridge Crystal Structure Data Centre. Sequence databases include the Protein Identification Resource (National Biomedical Research Foundation), GENBANK (Los Alamos National Laboratory), EMBL (European Molecular Biology Laboratory) and SBASE (International Center for Genetic Engineering and Biotechnology). Denied alignment databases, in which 3D structure and amino acid sequence have been correlated, include NRL-3D (U.S. Naval Research Lab), HSSP (EMBL), 3D-ALI (EMBL), FSSP (EMBL), and the Overington database (J.P. Overington, Pfizer Central Research). For complete addresses see Table 2 in Johnson et al (1994).

The basic approach is to (1) identify related sequences and structures; (2) identify structurally equivalent residues; (3) model structurally conserved regions (SCRs); and (4) model structurally variable regions (SVRs). The model of the SCRs acts, to a greater or lesser degree, as a constraint in the modeling of the SVRs. Because the core residues are usually more structurally conserved than surface residues, they are usually modeled first. For similar reasons, helices and strands are usually modeled before loops. Typically, the main chain (Cα atom) conformation is determined first, and then the side chain conformations. Modeling steps may be iterated to arrive at successively improved approximations of the true structure. Typically, the predicted structures are more accurate for protein cores than for protein loops.

It is not necessary that more than one 3-D structure be available for model building. However, if the 3-D structures of two or more homologous proteins are known, the accuracy of the model can be improved. Preferably, the 3-D structures are "weighted" to reflect the relatedness of the homologous protein to the protein of interest. One popular scheme is to weight by the square of the percentage sequence identity.

Moreover, information regarding homologous substructures of non-homologous proteins may be used in addition to, or even in lieu of, a 3-D structure of a homologous protein. See Jones et al (1986), Unger et al (1989), Claessens et al (1989), and Levitt (1992) for the building of models by combining "spare parts" from different proteins.

It is not necessary for a molecular biologist to be an expert in protein modeling, as several programs exist which automate the modeling process. These include COMPOSER (Tripos Associates).

If a 3-D structure is available for the binding partner, as well as for a binding protein of interest, molecular modeling software may be used to predict potential binding sites, or to predict the effect of a proposed mutation on a binding site, by attempting to "dock" the binding partner to the site. See, e.g., Guruprasad et al (1996) and Constantino et al (1996).

In general, within families of proteins of similar sequence and function, surface residues are more likely to vary than are interior residues. This is most likely because the surface residues are unlikely to be involved in interactions with other residues which are necessary to maintain the overall conformation of the protein.

Some surface residues are directly involved in the binding surface by which a protein exercises a particular binding activity. Mutation of such residues is likely to affect binding; however, it is not necessarily undesirable to make such mutations. For example, mutation of the binding site of a serine protease can alter what is bound, as opposed to simply rendering the protein inactive altogether.

The most reliable method of identifying the surface residues of a protein is to determine the protein's 3-D structure by X-ray diffraction. Even an incomplete 3D structure can be useful in designing mutants. Residues with high mobility, as evidenced by a higher than average crystallographic thermal factor, are those least susceptible to destabilizing mutations. See Alber et al (1987).

Although many amino acid substitutions can be made at surface positions with no adverse effects, substitutions at internal positions tend to be severely destabilizing. Within families of homologous proteins, the most conserved residues, apart from functional amino acids, are those which are buried.

The main contribution to the free energy of protein folding, and hence to protein stability, comes from burying hydrophobic side chains in the interior, thereby shielding them from solvent. Packing densities are typically high. In general, the ability of a protein to tolerate mutations which alter the volume of core residues is dependent more on the net change in the total core residue volume, then on the magnitude of the individual residue volume changes. In other words, an increase in the volume of one core position can compensate for a decrease in the volume of another core position. Preferably, the net change in the total core residue volume is not more than 10%, more preferably, not more than 5%. See Lim et al (1989) and Lim et al (1992).

In the absence of evidence to the contrary, all residues identified as interior residues may be assumed to be part of a single core. However, if it is likely that the protein folds to form several distinct cores, the above-stated volume conservation rule should be applied separately to each core.

Amino acids differ in terms of their propensity to be buried residues. The following table shows, for each residue, the percentage which were in buried positions, based on a study of the 3D structures of unrelated proteins:

| Amino Acid | % Buried |
| --- | --- |
| Gly | 36 |
| Ala | 38 |
| Val | 54 |
| Ile | 60 |
| Leu | 45 |
| Phe | 50 |
| Pro | 18 |
| Ser | 22 |
| Thr | 23 |
| Cys | 48 |
| Met | 40 |
| Tyr | 15 |
| Trp | 27 |
| His | 17 |
| Asn | 12 |
| Gln | 7 |
| Asp | 15 |
| Glu | 18 |
| Lys | 3 |
| Arg | 1 |

The makeup of the buried core of a protein is dependent, not only on the propensity of each amino acid, if present, to be buried, but also on the overall frequency of occurrence of that amino acid in the protein. The most commonly buried residues are, in descending order, Val, Gly, Leu, Ala, Ile and Ser.

Lim et al (1992) reported that replacing a single hydrophobic amino acid (Leu, Val) in the protein core with a hydrophilic amino acid (Asn, Gln) prevented the complete folding of the protein and destroyed biological activity.

Buried Cys, (—S—S— form), Asp, Gly, His, Pro, and Trp are more than 70% likely to be unchanged in a homologous protein. Therefore, if these residues occur in a buried position in the protein of interest it is preferable to leave them unchanged. Their conservation is probably explainable as follows: Cys (disulfide bonding), Asp (charged but rigid side chain), Gly (chain flexibility), His (charged and uncharged states both available at physiological pH), Pro (unique chain geometry), and Trp (largest side chain).

The other residues, with the exception of Met, are 40–60% likely to left unchanged when buried (Met is unchanged only 26% of the time, but it is 25% likely to be replaced by Leu).

The following buried residue substitution probabilities exceed 10%:

Ala→Val, Glu→Gln, Phe→Leu, Ile→Leu, Ile#Val, Lys→Arg, Leu→Ile, Leu→Val, Met#Leu, Met→Val, Asn→Asp, Asn→Ser, Arg→Lys, Arg→Gln, Ser→Ala, Thr→Ser, Val→Ile, Val→Leu, Tyr→Phe, Cys(—SH) →Ala.

These further substitutions have probabilities in the 5–10% range:

Ala→Ser, Asp→Asn, Glu→Arg, Glu→Val, Phe→Ile, Phe→Val, Phe→Tyr, His→Val, Leu→Phe, Met→Ala, Met→Ile, Gln→Glu, Gln→His, Gln→Met, Ser→Gly, Ser→Thr, Thr→Val, Val→Ala, Trp→Phe, Tyr→Leu, Cys (→SH)→Ser.

See Overington et al (1992), Table 5.

The most consistent exchange groups appear to be (Arg, Lys), (Leu, Ile, Met, Val, Phe), and (Ser. Thr, Ala). However, Ala and Val appear to be fairly promiscuous.

In general, therefore, it is preferable to avoid mutating buried residues at all. However, if they are mutated, one should limit the overall change in the volume of the core, and most preferably should limit the mutation to the replacement of one residue with another whose typical substitution probability exceeds zero, more preferably is at least 5%, and most preferably at least 10%. Mutation of buried Cys(—S—S), Asp, Gly, His, Pro and Trp should be avoided, absent justification by other evidence. The safest core mutations are exchanges of one hydrophobic amino acid for another, and of Arg for Lys (or vice versa).

Nonetheless, judicious mutation at internal residues may be used to improve protein stability. Such mutations could introduce additional stabilizing interactions (hydrogen bonds, ion pairs) compatible with the native structure, or could reduce the mobility of nearby interacting groups by replacing smaller amino acids with larger ones, or linear side chains with branched or aromatic ones. See Alber (1987).

The most useful information for determining which residues are safely mutatable in muteins is knowledge of the sequence of pcCMT proteins. The sequences of these homologous pcCMT proteins may then be aligned, and residues which are not conserved are more likely to be safely mutatable. The degree of confidence which one has as to the tolerance of a residue to mutation is a function of the degree of variation of amino acid type at that site among the protein family, as well as the extent to which all of the proteins in the family, despite their differences, retain the desired activity.

While studies of homologous proteins are useful in identifying sites which, by virtue of their variability, are likely to be tolerant of mutation, it is less certain that sites which are strongly conserved are necessarily invariant. Random mutagenesis studies have indicated that proteins are able to accommodate, both structurally and functionally, a far greater variety of mutations than occur naturally.

Cognate proteins are homologous proteins, expressed in a different species of organism, which perform the same biological function as that performed by the protein of interest, although they may differ in activity, specificity, timing of expression, etc. Such cognate pcCMT proteins from other mammals can be obtained upon possession of the human pcCMT cDNA or genomic DNA as the first identified mammalian pcCMT gene (the "starting DNA") encoding the pcCMT protein of interest (the "starting protein") which greatly facilitates the isolation of cognate mammalian proteins.

In one embodiment, the human pcCMT DNA, or a fragment thereof, is used as a hybridization probe to screen a cDNA or genomic DNA library for clones containing inserts which encode either the entire cognate protein, or a recognizable fragment thereof. The minimum length of the hybridization probe is dictated by the need for specificity. The library is preferably derived from the genomic DNA or mRNA of mammalian cells which are likely to be relatively high producers of pcCMT.

If the mammal in question is known to have substantially different codon preferences from that of human cDNA or genomic DNA, a synthetic hybridization probe may be used which encodes the same amino acid sequence but whose codon utilization is more similar to that of the DNA of the target mammal. Alternatively, the synthetic probe may employ inosine as a substitute for those bases which are most likely to be divergent, or the probe may be a mixed probe which mixes the codons for the source DNA with the preferred codons (encoding the same amino acid) for the target mammal.

By routine methods, the Tm of a perfect duplex of starting DNA is determined. One may then select a hybridization temperature which is sufficiently lower than the perfect duplex Tm to allow hybridization of the starting DNA (or other probe) to a target DNA which is divergent from the starting DNA. A 1% sequence divergence typically lowers the Tm of a duplex by 1–2° C., and the DNAs encoding homologous proteins of different species typically have sequence identities of around 50–80%. Preferably, the library is screened under conditions where the temperature is at least 20° C., more preferably at least 50° C., below the perfect duplex Tm. Since salt reduces the Tm, one ordinarily would carry out the search for DNAs encoding homologous proteins under low salt hybridization conditions, e.g., <1M NaCl.

For the use of probes to identify homologous genes in other species, see, e.g., Schwinn et al (1990) (hamster 67-bp cDNA probe vs. human leukocyte genomic library; human 0.32 kb DNA probe vs. bovine brain cDNA library, both with hybridization at 42° C. in 6xSSC); Jenkins et al (1990) (Chicken 770-bp cDNA probe vs. human genomic libraries; hybridization at 40° C. in 50% formamide and 5xSSC non-stringent washing); Murata et al (1992) (1.2-kb mouse cDNA probe v. human eosinophl cDNA library; hybridization at 65° C. in 6xSSC); Guyer et al (1990) (2.95-kb human genomic DNA probe vs. porcine genomic DNA library; hybridization at 42° C. in 5xSSC).

Hybridization conditions for hybridizing to a homologous sequence which encodes a protein which has, for example, at least 70% identity to the amino acid sequence encoded by the probe sequence (i.e., SEQ ID NO:5) is well within the skill of those in the art, particularly in view of numerous reference texts on hybridization, such as Ausubel (1987–1998), Chapter 6.

If human pcCMT and the cognate mammalian protein are immunologically cross-reactive, antibodies raised against the human pcCMT may be used in a second approach to identifying genes encoding cognate mammalian proteins. In that approach the library is caused to express the polypeptides encoded by the cloned inserts, and the expression products are screened using the antibodies raised against human pcCMT. If the proteins are cross-reactive, the cognate mammalian protein will be detected and the corresponding gene can be recovered.

In order to derive guidance from the sequences of cognate pcCMT proteins, a homology or alignment score for each possible alignment is calculated, and the highest such score for each pair of cognate pcCMT proteins is determined. Global alignment algorithms consider both complete sequences in generating similarity scores for a given alignment, and, in general, allow "gapping". They are most appropriate when the sequences are known or expected to be similar over their entire length. Local alignment algorithms, however, search for similar fragments of two sequences, and, in general, do not allow gaps. They are useful in locating common subdomains between long sequences that otherwise share little similarity.

Binding sites may also be identified by mutagenesis strategies designed to locally perturb the protein. One such strategy is alanine scanning mutagenesis. In this technique, all non-alanine residues of the protein (or of a region of the protein suspected to contain the binding site are replaced, one-by-one, with alanine, yielding a collection of single substitution mutants. Alanine is used because (1) it is the most common amino acid residue in proteins, (2) it has a small side chain, and therefore is not likely to sterically hinder other residues, and (3) its side chain (—$CH_3$) does not form H-bonds, but is not especially hydrophobic. Cunningham and Wells (1989) conducted an Ala scanning mutagenesis study of residues 2–19, 54–74, and 167–191 in hGH. A total of 62 Ala mutations were produced. Of these, fourteen mutants could not be produced in quantities sufficient for affinity testing. Presumably, these mutations globally destabilized the protein, rendering it vulnerable to proteolysis. Eleven mutants seemingly enhanced binding, although it is unclear which improvements were significant. Of the remaining 37 mutants, only four impaired binding by 10-fold or more, and only nine by 5-fold or more. See generally Genentech, WO90/04788.

For other uses of Ala-scan mutagenesis, see Yu et al (1995) (complete scan of a single disulfide derivative of the 58-residue protein BPTI); Allen et al (1987) (Ala-scan of residues 52–61 of hen egg white lysozyme); Ruf et al (1994) (Ala-scan of residues other than Gly, Pro and Cys; multiple Ala mutants examined first, then single Ala mutants); Williams et al (1995) (Ala-scan in insulin receptor of (1) charged amino acids, (2) aromatic residues, and (3) residues adjacent to (1) or (2), other than prolines, cysteines, or potential N-linked glycosylation sites); Kelly et al (1993) (Ala-scan of antibody CDR). Ala-scanning mutagenesis may be applied to all residues of a protein, or to residues selected on some rational basis, such as amino acid type (e.g., charged and aromatic residues), degree of variability in a homologous protein family, or relevance to function as shown by homologue-scanning mutagenesis.

Preferably, further mutations (especially non-conservative mutations) are made at sites where an alanine substitution does not worsen the activity of interest by more than 20-fold, more preferably, by more than 10-fold, even more preferably, by more than 5-fold, still more preferably, by more than 2-fold. Most preferably, mutations are made at sites at which an alanine substitution improves activity.

Preferably, if multiple mutations are made, the expected (additive) effect of the mutations is one which does not worsen the activity more than 10-fold, more preferably, by more than 5 fold, still more preferably, by more than two fold. Most preferably, the expected effect is to improve activity. The expected effect of a conservative substitution is the effect of that mutation as a single substitution if known, or otherwise neutral. The expected effect of a non-conservative substitution is the effect of that mutation as a single substitution if known, or otherwise the effect of a single substitution of a different residue of the same exchange group as the actual replacement residue, if known, or otherwise the effect of a single Ala substitution.

Another approach is homologue-scanning mutagenesis. This involves identifying a homologue which can be distinguished in an activity assay from the protein of interest, and screening mutants in which a segment of the protein of interest is replaced by corresponding segments of the homologue (or vice versa). If the replacement alters the activity of the modified protein, the segment in question presumably contributes to the observed difference in activity between the protein of interest and the homologous protein, and comparison of the interchanged segments helps to explain the character of the binding site involved in that activity. For example, segments of prolactin, which does not bind the GH receptor, have been used to replace segments of growth hormone, which does. If a substitution disrupts GH binding, it implies that the replaced segment was part of the GH receptor binding site, and one may then focus on how the replaced and replacing segments differ. See WO90/04788.

If a residue is determined to be a part of the binding site, one may prepare all possible single substitution mutants of that site.

It is possible to incorporate two or more tolerable mutations into a protein.

Generally speaking, as a first approximation, it is reasonable to assume that the effect of two mutations will be additive in nature. See Wells (1990); Sandberg and Terwilliger (1993); Gregoret and Sauer (1993); Schreiber and Fersht (1995); et al (1993); Lowman et al (1991); Lin et al (1994); Venkatachalam et al (1994); Akasako et al (1995); Behravan et al (1991); Lin et al (1994); Zuckermann et al (1992).

Non-additive effects are more likely to occur between residues that are in Van der Waals contact with each other. See Sandberg and Terwilliger (1993). According to Schreiber and Fersht (1995), non-additive effects are more likely to occur between residues less than 7 Å apart (10 Å in the case of charged residues). The effect of a second mutation on a first one may be synergistic, additive, partially additive, neutral, antagonistic, or suppressive. Long range but low magnitude departures from additivity may occur reasonably often, see LiCata and Ackers (1995), but do not significantly impair the value of multiple mutation in protein engineering.

Gregoret et al (1993) assumed that, under selective conditions, the frequency of occurrence of a mutation in an active mutant was an indication of whether the mutant conferred resistance, and found that an additive model (multiplying the mutational frequencies of a pair of single Ala substitution mutants) was about 90% effective in predicting the activity class of a binomial (multiple Ala substitution) mutant.

The most common reason for combining mutations is to benefit from their additive or synergistic effect in combination. For example, if a mutation has both favorable and unfavorable activities, it may be possible to combine it with a second mutation that neutralizes the unfavorable activity of the first mutation.

One use of multiple mutation is to achieve, by combining mutations which individually have a small but favorable effect on activity, a mutant with a more substantial improvement in activity. It is not necessary that the mutations be strictly additive; it is sufficient that they be at least partially additive for the combination to be advantageous. See Blacklow et al (1991) (improved catalytic effectiveness of triosephosphate isomerase); Akasako et al (1995) (multiple thermostabilizing mutations in ribonuclease HI); Lowman et al (1991) (HGH-receptor binding properties of human placental lactogen improved about 500-fold by five simultaneous, mutations, with "reasonably additive" effects); Lowman and Wells (1993) (HGH-receptor binding properties of HGH improved about 400-fold by combination of 15 substitutions. Sandberg and Terwilliger (1993), reported that there was only a weak correlation between changes in DNA binding protein stability and changes in DNA binding affinity, and hence that it was possible to combine mutations so as to selectively change one property without changing the other.

Watanabe et al (1994) suggests that increasing the number of proline residues, especially at second sites of beta turns and N-caps of alpha helces, increases the thermostability of the protein in an additive manner.

Gloss et al (1992) converted all cysteines of a protein to alanine. They point out that this cysteine-free mutant provides a platform onto which uniquely placed cysteine residues may be engineered, thereby allowing the introduction of unnatural amino acids through exploitation of the unique reactivity of the thiol group.

The interactivity of two residues is generally determined by preparing both single substitution mutants as well as a double substitution mutant, and determining whether the effects are additive or not. Therefore, if single Ala substitutions have been shown to favorably or unfavorably affect activity, one may prepare a double Ala mutant and compare its activity to that of the single substitution mutants. While it is certainly possible that two mutations which, by themselves, do not affect activity, may do so when combined, this is unlikely, especially if the sites are not close together.

While in theory one could prepare all possible double Ala mutants, this would mean preparing N(N−1) mutants, where N was the number of non-Ala residues in the protein. In general, one would limit the double substitution studies to sites known to favorably affect the activity. Possibly, one would also consider sites which were strongly unfavorable (to look for antagonistic interactions).

Another approach is binomial Ala-scanning mutagenesis. Here, one constructs a library in which, at each position of interest of a given protein molecule, the residue is randomly either the native residue, or Ala. See Gregoret and Sauer (1993). If it is feasible to screen a library of $10^{10}$ mutants, then the combined effects of up to 30 different Ala substitutions ($2^{27} \sim 10^{10}$) can be studied in one experiment. It should be noted that the Ala:non-Ala ratio at each position may be, but need not be equal. The choice made for this ratio will determine the degree of substitution will predominate, according to a binomial distribution.

If the protein is too large for all sites of interest to be sampled by binomial Ala-scanning mutagenesis in a single experiment, one may divide the protein into segments and subject each segment in turn to such mutagenesis, and then, as a cross-check, similarly mutate one residue from each segment.

Even when mutations are not additive in effect, this is not necessarily undesirable. Green and Shortle, (1993) reported that mutations which individually reduced stability, when not additive in their effects, were almost exclusively sub-additive, i.e., the reduction in stability was less than that expected by summing the individual destabilizations. This is credited to an overlap of the "spheres of perturbation" surrounding the two mutations. Ballinger et al (1995) reported that a combination subtilisin BPN' mutant had a larger than additive shift in specificity toward dibasic substrates, which is a desirable change.

Certain multiple mutations are worthy of special comment.

Primary shifts: In a primary shift the residue at position n becomes the replacement amino acid at position n+s, or vice versa. For example, instead of Cys at 30, one might have Cys at 31. The result is a mere displacement, rather than a loss, of the amino acid in question. In a primary shift, s (the shift distance) is most often equal to one, but may be two, three or more. The greater the value of s, the more the shift resembles an ordinary double mutation.

Primary transpositions: In a primary transposition, the residues at positions n and n+s in the primary amino acid sequence are swapped. Such swaps are less likely to perturb the protein than the individual replacements, examined singly, might suggests. A primary transposition is, in effect, a combination of two complementary shifts.

Secondary Transposition: Here, two amino acids which interact as a result of the folding of the protein are swapped. A classic example would be members of a salt bridge. If there is an Asp in one segment forming a salt bridge with a Lys in another segment, the Asp and Lys can be swapped, and a salt bridge can still form.

Coordinated Replacement: Here, replacement of residue x is coordinated with replacement of residue y. Thus, replacement of one Cys may be coordinated with replacement of a second Cys with which it otherwise forms a disulfide bond, and if one amino acid of a pair forming a salt bridge is replaced by an uncharged a.a., the other may likewise be replaced.

Techniques of detecting coordinated amino acid changes in families of homologous proteins are discussed in Altschuh et al (1988).

Primary shifts, primary transpositions, secondary transpositions and coordinated replacements are more likely to be tolerated than other multiple mutations involving the same individual amino acid changes.

Figure 4A:
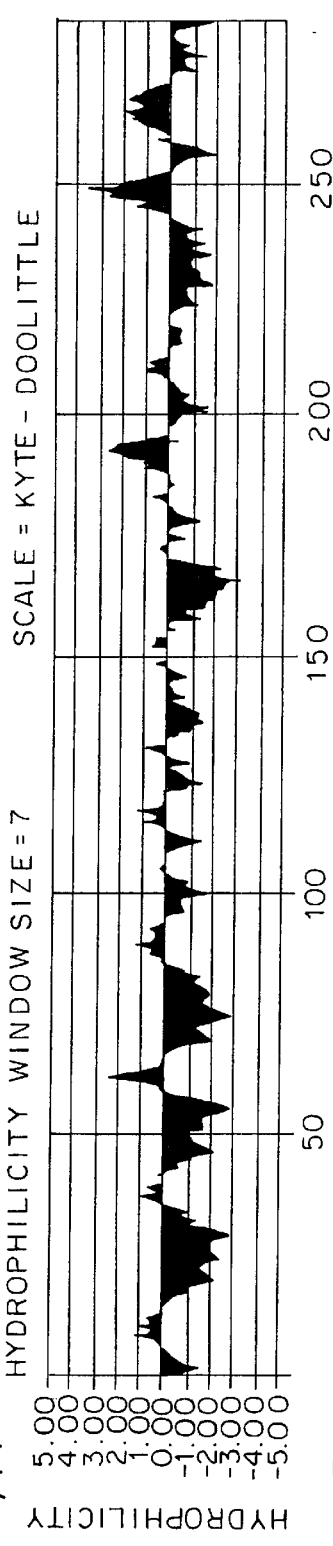
FIGS. 4A–GG show plot analysis of pcCMT structure where
Figure 4B:
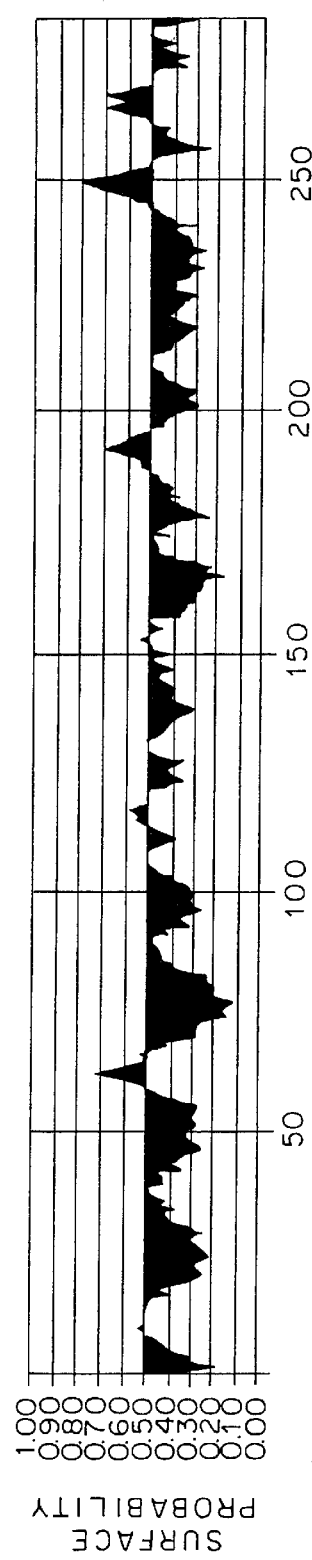
FIG. 4B shows surface probability.
Figure 4C:
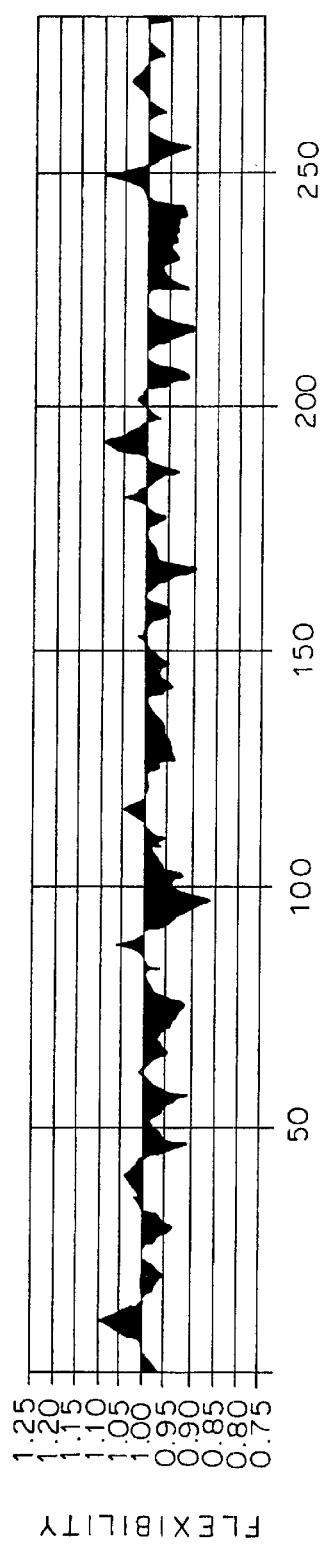
FIG. 4C shows flexibility.
Figure 4D:
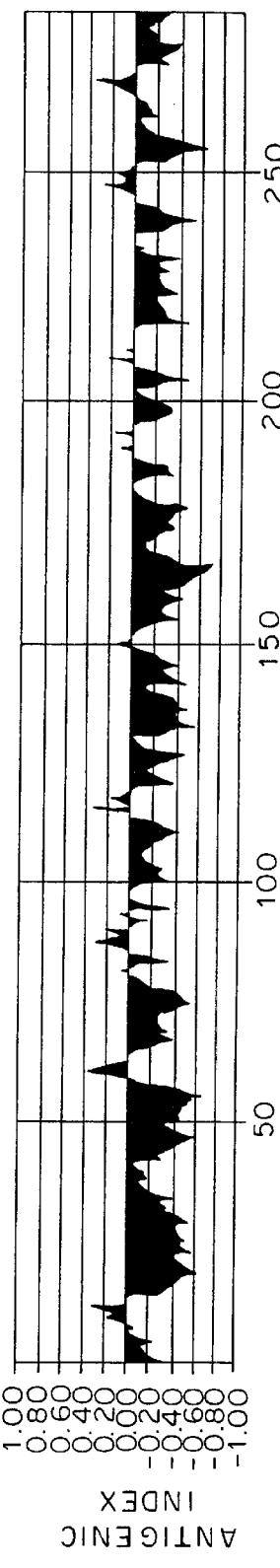
FIG. 4D shows antigenic index.
Figure 4E:
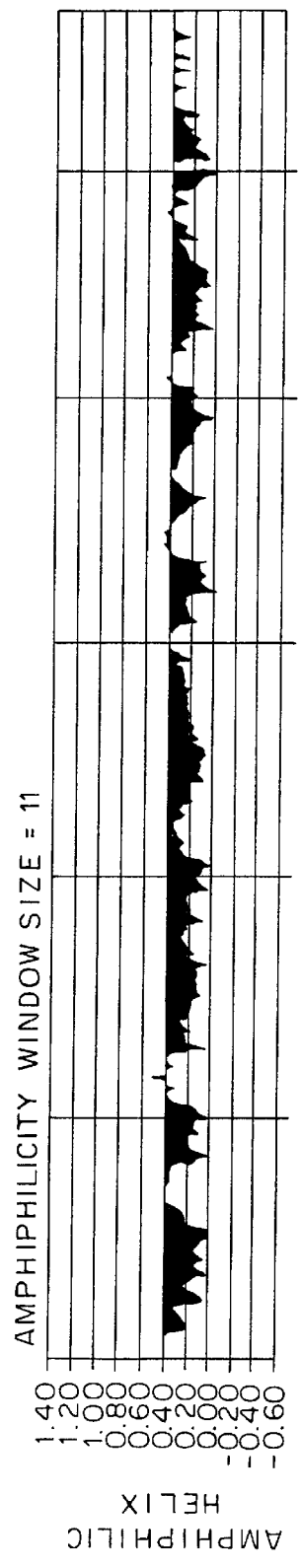
FIG. 4E shows amphiphilic helix.
Figure 4F:
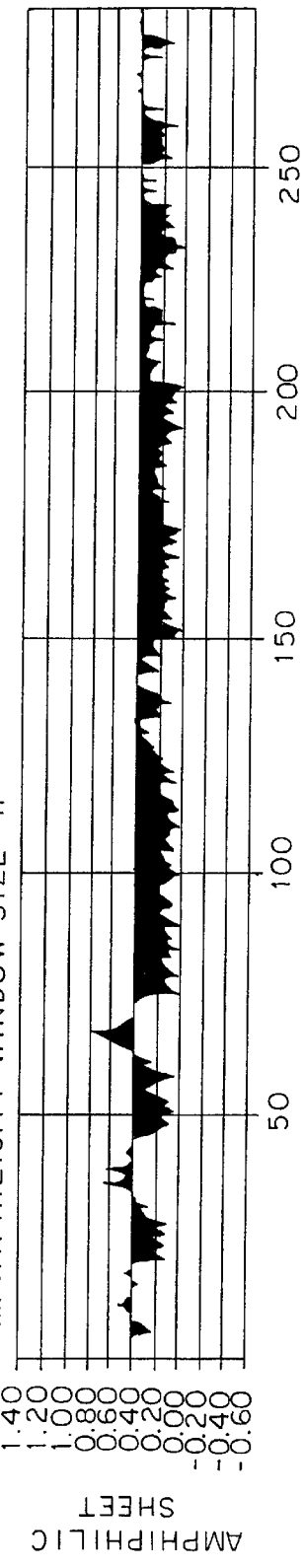
FIG. 4F shows amphiphilic sheet.
Figure 4G:
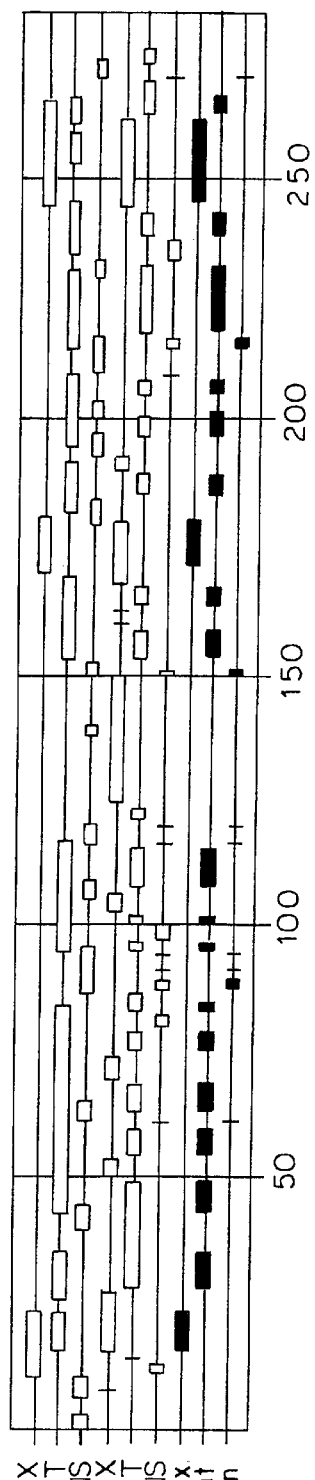
FIG. 4G shows secondary structure structure, all plotted against pcCMT amino acid number.

The amino acid sequence alignment for homology between the deduced amino acid sequence of human pcCMT and related genes and sequences is shown in FIG. 2. Amino acid identity between human pcCMT and other gene products in FIG. 2 is indicated with dark shading. Those of skill in the art reviewing the amino acid sequence alignment shown in FIG. 2 will understand the positions where amino acid substitutions, deletions, additions can be made with the highest expectation of retaining the enzymatic activity of the native enzyme. For instance, it can be seen at amino acid positions where the areas of dark shading are mixed with areas of no shading in FIG. 2, or in which there is no dark shading, that conservative amino acid substitutions may be predicted to still substantially retain the carboxyl methyltransferase activity of the human pcCMT, especially where there are alternative amino acids shown in the non-shaded area at a conserved residue position having like properties in protein structure. Amino acid residues at positions in which there is no dark shading show no conservation, (e.g., identity, homology), and in which the charge, hydrophobicity, steric properties, etc., of the amino acid residue are predicted not to substantially affect the enzymatic activity and protein structure of pcCMT, can be substituted with virtually any of the common amino acids. Secondary structure prediction (FIG. 4G), such as routinely obtained by a Chou-Fasman analysis or other similar analysis, and the other structural predictions shown in FIGS. 4A–4F provide those of skill in the art with further information on what amino acids may be appropriate substitutes at a particular residue position.

Preferably, the muteins of SEQ ID NO:5 have at least 85% identity to SEQ ID NO:5, and more preferably at least 90% identity, and most preferably at least 95% identity while substantially retaining the carboxyl methyltransferase activity of the human pcCMT of SEQ ID NO:5.

Examples of production of amino acid substitutions in proteins which can be used for obtaining muteins of human pcCMT for use in the present invention include any known method steps, such as presented in U.S. Pat. No. RE 33,653, U.S. Pat. Nos. 4,959,314, 4,588,585 and 4,737,462, to Mark et al; U.S. Pat. No. 5,116,943 to Koths et al, U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

At the genetic level, these muteins are generally prepared by site-directed mutagenesis of nucleotides in the DNA encoding the human pcCMT, thereby producing DNA encoding the mutein, and thereafter synthesizing the DNA and expressing the polypeptide in recombinant cell culture.

The muteins typically exhibit the same or increased qualitative biological activity as the naturally occurring protein, Ausubel et al (1987–1997); Sambrook et al (1989).

Preparation of a human pcCMT mutein in accordance herewith, or an alternative nucleotide sequence encoding the same polypeptide but differing from the natural sequence due to changes permitted by the known degeneracy of the genetic code, can be achieved by site-specific mutagenesis of DNA. Site-specific mutagenesis allows the production of muteins through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 complementing nucleotides on each side of the sequence being altered. In general, the technique of site-specific mutagenesis is well known in the art, as exemplified by publications such as Adelman et al (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al (1981), the disclosure of which is incorporated herein by reference. These phage are readily available commercially and their use is generally well known to those skilled in the art. Alternatively, plasmid vectors that contain a single-stranded phage origin of replication (Vieira et al, 1987) may be employed to obtain single-stranded DNA.

In general, site-directed mutagenesis in accordance herewith is performed by first obtaining a single-stranded vector that includes within its sequence a DNA sequence that encodes the relevant polypeptide. An oligonucleotide primer bearing the desired mutated sequence is prepared synthetically by automated DNA/oligonucleotide synthesis. This primer is then annealed with the single-stranded DNA-sequence-containing vector, and subjected to DNA-polymerizing enzymes such as $E.$ $coli$ polymerase I Klenow fragment, to complete the synthesis of the mutation-bearing strand. Thus, a mutated sequence and the second strand bears the desired mutation. This heteroduplex vector is then used to transform appropriate ceils, such as $E.$ $coli$ JM101 cells, and clones are selected that include recombinant vectors bearing the mutated sequence arrangement.

After such a clone is selected, the mutated human pcCMT may be removed and placed in an appropriate vector, generally a transfer or expression vector of the type that may be employed for transfection of an appropriate host.

A recombinant DNA molecule encoding the mammalian pcCMT according to the present invention can be obtained by cDNA cloning using the characterized human pcCMT gene as the starting DNA to isolate cognate mammalian pcCMT as disclosed above in the discussion on cognate mammalian proteins. This recombinant DNA is then incorporated into a replicable expression vector such as a plasmid capable of autonomous replication or chromosomal integration in recipient host cells. Standard reference works setting forth the general principles of recombinant DNA technology include Ausubel et al (1987–1997), Watson et al (1987); Darnell et al (1986); Lewin, (1985); Old et al (1981); and Sambrook et al (1989). These references are hereby incorporated by reference.

In order to be capable of expressing the mammalian pcCMT, an expression vector should have specific nucleotide sequences containing transcriptional and translational regulatory information linked to the DNA coding for the mammalian pcCMT in such a way as to permit gene expression and production of the protein. First, in order for the gene to be transcribed, it must be preceded by a promoter recognizable by RNA polymerase, to which the polymerase binds and thus initiates the transcription process.

A DNA is said to be "capable of expressing" a polypeptide, such as pcCMT, if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The regulatory regions needed for gene expression in general include a promoter region as well as the DNA sequences which, when transcribed into RNA, will signal the initiation of protein synthesis. Such regions will normally include those 5'-non-coding sequences involved with initiation of transcription and translation. There are a variety of promoters in common use for high level protein expression in mammalian and insect cell systems.

The DNA molecule containing the nucleotide sequence coding for mammalian pcCMT of the invention, and the operably linked transcriptional and translational regulatory signals can be inserted into a vector which either transiently expresses the mammalian pcCMT in host cells or is capable of integrating the desired gene sequences into the host cell chromosome. In order to be able to select the cells which have stably integrated the introduced DNA into their chromosomes, one or more markers which allow for selection of host cells which contain the expression vector is used. The marker may provide for prototropy to an auxotrophic host, biocide resistance, e.g., resistance to antibiotics, or heavy metals, such as copper, or the like. The selectable marker gene can either be directly linked to the DNA gene sequences to be expressed, or introduced into the same cell by cotransfection. Additional elements may also be needed for optimal synthesis of mRNA. These elements may include splice signals, as well as transcription promoters, enhancers, and termination signals. cDNA expression vectors incorporating such elements include those described by Okayama et al (1983).

Expression vectors which are capable of transiently expressing a high level of the desired protein when transfected into eukaryotic host cells, are well-known in the art and are generally either publicly available or commercially available from molecular biology suppliers (e.g., plasmid pcDM8, is available from Invitrogen, San Diego, Calif. ). Once the vector or DNA sequence containing the construct (s) has been prepared for expression, the expression vector may be introduced into an appropriate host cell by any variety of suitable means, such as transformation, transfection, lipofection, conjugation, protoplast fusion, electroporation, calcium phosphate precipitation, direct microinjection, etc.

Eukaryotic host cells can be mammalian cells, e.g., human cells, monkey (COS cells), mouse and Chinese hamster ovary (CHO) cells, because they provide post-translational modifications to protein molecules including correct folding, correct disulfide bond formation as well as glycosylation at correct sites. However, insect cells, e.g., baculovirus, can overproduce polypeptides and can also carry out post-translational peptide modifications including glycosylation. Ectopic protein expression in COS, CHO and insect cells are well known in the art and protocols, such as those provided in Ausubel et al (1987–1997), sections 16.9–16.14, on expression of proteins in insect cells using baculovirus vectors and in mammalian cells, can be suitably used. The transfected host cells expressing mammalian pcCMT are harvested to obtain membrane preparations for determining the carboxyl methyltranferase activity as described in Philips et al (1995b).

The method of screening for inhibitors of pcCMT as therapeutic antiproliferative and antiinflammatory agents according to the present invention involves providing a membrane preparation, incubating the membrane preparation with substrate, such as described by Philips et al (1995b) in the presence or absence (control) of a potential pcCMT inhibitor, and determining whether the level of carboxyl methyltransferase activity is blocked/inhibited by the potential inhibitor relative to the control. While the use of membrane preparations of cells associated with a high level of ectopic protein expression offers the advantage of high expression and activity levels in these membrane preparations relative to the low level of carboxyl methyltransferase that are present endogenously in these membrane preparations, membrane preparations with endogenous levels may also be used. Generally, aside from a low endogenous level of pcCMT activity in the membrane preparation, the prenylcysteine carboxyl methyltransferase, which is present in the membrane preparation used to screen for pcCMT inhibitors according to the method of the present invention, is not native to the source of the membrane preparation.

One can assay for potential prenylcysteine carboxyl methyltransferase (pcCMT) inhibitors in at least two ways. In a first method, cellular membranes or artificial liposomes containing pcCMT are used as a source of enzyme, small molecules such as N-acetyl-S-trans-farnesyl-L-cysteine (AFC), peptides that terminate in a prenylcysteine residue, or prenylated proteins (e.g., rhoA) serve as substrates, and S-adenosyl-L-methionine (SAM) radiolabeled on the methyl group is added as the methyl donor. pcCMT enzymatic activity can then be directly determined by measuring the transfer of the radiolabeled methyl group to the substrate. Candidate pcCMT inhibitors can be included in the reaction and extent of inhibition measured. A high throughput system based on this assay can be designed (e.g., microtiter plate assay system) to screen a large number of compounds for potential inhibitors. Although endogenous pcCMT (e.g., membranes isolated from HL60 cells) could, in principle, be used as the source of enzyme in this assay, the use of recombinant human pcCMT offers several advantages. Most important is the ability to overexpress the recombinant enzyme ectopically in mammalian cells such as CHO or COS (as demonstrated in Dai et al) or in insect cells such as sf9 such that the membrane harvested from the transfected cells offers a markedly enriched, homogeneous, reproducible, and replenishable source of enzyme. Moreover, unlike the endogenous activity that may represent more than one enzyme, the overexpressed recombinant enzyme is fully characterized at the molecular level and would therefore lend itself to mutational analysis useful in rational drug design.

The second method would take advantage of the biology of a model genetic organism, S. cerevisiae. In contrast to the inhibitor screen described above that relies directly on biochemical activity, the S. cerevisiae screen would have a biological readout: the inhibition of mating competence. The ability of MATa strains of S. cerevisiae to mate with MATα strains is absolutely dependent on the production of biochemically active a factor from MATa strains. MATa strains of S. cerevisiae that lack a functional pcCMT, i.e. ste14 mutants, are unable to mate (sterile) because the a factor that they produce cannot be carboxyl methylated on prenylcysteine, a modification required for biological activity. The laboratory of the present inventors has shown (Dai et al) that the human pcCMT gene can functionally substitute for the S. cerevisiae STE14 gene (complementation). Thus, as a method to screen for inhibitors of human pcCMT, a strain of MATa S. cerevisiae that has the human pcCMT gene substituted for the endogenous STE14 locus can be constructed by standard techniques (R. Rothstein, *Methods in Enzymology* 194:281–301, 1991). This strain would then be competent for mating with MATα cells. Standard mating assays (Sprague, Jr, 1991) could then be employed in the presence or absence of potential inhibitors of pcCMT. A potential pcCMT inhibitor would then be scored as a compound that blocked the mating of the MATa strain engineered to contain the human pcCMT gene with a MATα tester strain. The standard assays for mating competence include prototrophic growth of diploids on media non-permissive for either haploid strain or assays of a factor activity such as the halo assay whereby a factor produced by a patch of MATa cells inhibits the growth of nearby MATα tester cells spread as a lawn. The advantage of this screen is that it is exceedingly cheap and simple and therefore perfectly suited to high throughput screening. The anti-pcCMT activity of any potential inhibitor identified by the S. cerevisiae mating screen could then be verified with the biochemical assay described above.

An embodiment of a method of screening for inhibitors of pcCMT using membrane preparations according to the present invention is described in Example 2, where a biotinylated and prenylated peptide substrate for pcCMT, a labeled co-factor, and a membrane preparation containing pcCMT are incubated together in an avidin-coated or streptavidin-coated multiwell dish. The biotinylated substrate is bound to the avidin-coating and the action of carboxyl methyltransferase activity on the substrate in the presence of labeled co-factor generates a radiolabeled product which can be separated from the labeled co-factor by washing. The amount of labeled product is then detected, e.g., the level of radiolabeled product in avidin- or streptavidin-coated well is determined by measuring cpm, relative to a control. This format allows for rapid high throughput screening for pcCMT inhibitors. Previously published methods of screening for enzyme inhibitors involve the use of test tubes where the product is extracted into heptane and then measured following a tedious demethylation procedure (Pillinger et al, 1994; Shi et al, 1992).

As previously disclosed, it is intended that the membrane preparations containing a pcCMT encompass artificial membrane preparations, such as phospholipid vesicles/liposomes, which reconstitutes membrane extracted pcCMT. A preferred method of reconstituting extracted pcCMT into liposomes is described in Philips et al (1995b) where pcCMT extracted from membranes with detergent was reconstituted in the presence of diacylphosphatidylcholine and an anionic phospholipid. Residual detergent in the sample was removed with Extractigel (Pierce), a detergent removing gel.

Small prenylcysteine analogs, such as N-acetyl-S-trans,trans-farnesyl-L-cysteine (AFC) and N-acetyl-S-all-trans-geranylgeranyl-L-cysteine (AGGC), are known to be substrates for pcCMT as well as inhibitors of the carboxyl methylation activity of pcCMT (Volker et al, 1995). Other potential inhibitory compounds can be more readily and reliably screened according to the method of the present invention in membrane preparations where a high level of ectopically expressed pcCMT is localized.

Once pcCMT inhibitors are identified and isolated according to the method of the present invention, techniques that are well-known and commonly used by pharmaceutical companies in drug development may be used to provide stability, enhance cell penetration, the design peptidomimetic inhibitors, etc., such as along the lines of the development of farnesyl-protein transferase inhibitors (Gibbs et al, 1996; Koblan et al, 1996). It is also contemplated that peptides or fragments of pcCMT may serve as an inhibitor of carboxyl methylation in the localization and function of membrane proteins, such as Ras, when overexpressed in the cell. The presence of such peptides in the cytosol may serve as antagonists and prevent the carboxyl methylation. Peptides or fragments of pcCMT can be readily generated for screening by removing successive residues from either or both the N-terminus or C-terminus of pcCMT, or from peptides obtained thereof by enzymatic or chemical cleavage of the polypeptide.

While the most important utility of the pcCMT of the present invention is as a tool in the search for inhibitors which could be used therapeutically in the treatment of inflammation or hyperproliferative disorders such as cancer, as discussed above, other utilities for such proteins would be readily apparent. For example, as the protein has enzymatic activity, it can be used in chemical processes in which carboxyl methylation of appropriate substrates is desired. Preparations of membranes containing pcCMT, in accordance with the present invention, may be used for carboxyl methylation of natural protein substrates, particularly when a high level of carboxyl methyltransferase activity from the ectopic expression of pcCMT is present in these membrane preparations. For example, proteins, which are substrates for pcCMT, i.e., Ras protein, nuclear lamins, G proteins, etc., have a prenylcysteine residue at the C-terminus. Such substrates may be methylesterified at the α-carboxyl group by a functional pcCMT to produce the functionally active form. Thus, membrane preparations containing high levels of mammalian pcCMT activity are well-suited for supplying quantities of functional Ras proteins, among others, that can be made commercially available. For a treatment of hyperproliferative and inflammatory disorders, gene therapy at the affected site, e.g., tumor, etc., may be used once a variant of pcCMT that would act as a dominant negative allele is identified.

The protein of the present invention is also useful to raise polyclonal or monoclonal antibodies by techniques well known in the art, one of which is described in the following example. Such antibodies are useful as research tools, for example, in localization of subcellular pcCMT or in otherwise identifying, the presence of the protein in situ or in vitro.

Antibodies to mammalian pcCMT, and to human pcCMT in particular, may also be used to disrupt the action of pcCMT, thereby treating disorders associated with inflammation or hyperproliferation. Additionally, the antibodies specific to pcCMT can be used in methods to detect the presence of, or measure the quantity of pcCMT in a cell or cell extract.

It should be understood that when the term "antibodies" is used with respect to the anti-pcCMT antibody, this is intended to include intact antibodies, such as polyclonal antibodies or monoclonal antibodies (mAbs), as well as proteolytic fragments thereof such as the Fab or F(ab')$_2$ fragments. Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (see Eshhar et al, 1990; Gross et al, 1989). Single chain antibodies can also be produced and used. Single chain antibodies can be single chain composite polypeptides having antigen binding capabilities and comprising a pair of amino acid sequences homologous or analogous to the variable regions of an immunoglobulin light and heavy chain (linked $V_H$-$V_L$ or single chain $F_v$). Both $V_H$ and $V_L$ may copy natural monoclonal antibody sequences or one or both of the chains may comprise a CDR-FR construct of the type described in U.S. Pat. No. 5,091,513 (the entire contents of which are hereby incorporated herein by reference). The separate polypeptides analogous to the variable regions of the light and heavy chains are held together by a polypeptide linker. Methods of production of such single chain antibodies, particularly where the DNA encoding the polypeptide structures of the $V_H$ and $V_L$ chains are known, may be accomplished in accordance with the methods described, for example, in U.S. Pat. Nos. 4,946,778, 5,091,513 and 5,096,815, the entire contents of each of which are hereby incorporated herein by reference.

A "molecule which includes the antigen-binding portion of an antibody," is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

In order to predict antigenic epitopes present in pcCMT, the amino acid sequence can be obtained from the cDNA of pcCMT can be inspected visually or analyzed by computer, for example, using the program of PEPTIDESTRUCTURE (Jameson et al, 1988). This program allows determination of hydropathicity values which are then used to determine which peptide sequences within the overall protein sequence are likely to be most immunogenic based on their potential secondary structure. Such peptides may be synthesized chemically, or alternatively, and preferably, by recombinant DNA methods.

Polyclonal antibodies are heterogeneous populations of antibody molecules derived from the sera of animals immunized with an antigen.

Monoclonal antibodies (mAbs) are a substantially homogeneous population of antibodies to specific antigens. MAbs may be obtained by methods known to those skilled in the art. See, for example Kohler and Milstein (1975); U.S. Pat. No. 4,376,110; Ausbel et al (1988); and Colligan et al (1993), the contents of which reference are incorporated entirely herein by reference. Such antibodies may be of any immunoglobulin class including IgG, IgM, IgE, IgA, GILD and any subclass thereof. The hybridoma producing the mAbs of this invention may be cultivated in vitro (see Example 3) or in vivo. High titers of mAbs can be obtained in in vivo production where cells from the individual hybridomas are injected intraperitoneally into pristane-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules, the different portions of which are derived from different animal species, such as those having a variable region derived from a murine mAb and a human immunoglobulin constant region. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al, 1984; Morrison et al, 1984; Boulianne et al, 1984; Cabilly et al European Patent Application 125.023 (published Nov. 14, 1984); Neuberger et al, 1985; Taniguchi et al, European Patent Application 171496 (published Feb. 19, 1985); Morrison et al, European Patent Application 173494 (published Mar. 5, 1986); Neuberger et al, PCT Application WO 8601533, (published Mar. 13, 1986); Kudo et al, European Patent Application 184187 (published Jun. 11, 1986); Morrison et al, European Patent Application 173494 (published Mar. 5, 1986); Sahagan et al (1986); Robinson et al, International Patent Publication WO 9702671 (published May 7, 1987); Liu et al (1987); Sun et al (1987); Better et al (1988); and Harlow et al, supra. These references are hereby incorporated by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may bear structural similarity to the original mAb which induced the anti-Id. Thus, by using antibodies to the idiotypic determinants of a mAb, it is possible to identify other clones expressing antibodies of identical specificity.

Accordingly, mAbs generated against the pcCMT protein of the present invention may be used to induce anti-Id antibodies in suitable animals, such as Balb/c mice. Spleen cells from such immunized mice are used to produce anti-Id hybridomas secreting anti-Id mAbs. Further, the anti-Id mabs can be coupled to a carrier such as keyhole limpet hemocyanin (KLH) and used to immunize additional Balb/c mice. Sera from these mice will contain anti-anti-Id antibodies that have the binding properties of the original mAb specific for a pcCMT protein epitope.

As mentioned above, the term "antibody" is also meant to include both intact molecules as well as fragments thereof, such as; for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al, 1983).

It will be appreciated that Fab and F(ab')$_2$ and other fragments of the antibodies useful in the present invention may be used for the detection and quantitation of pcCMT protein according to the methods disclosed herein for intact antibody molecules. Such fragments are typically produced by proteolytic cleavage, using enzymes such as papain (to produce Fab fragments) or pepsin (to produce F(ab')$_2$ fragments).

The antibodies, or fragments of antibodies, of the present invention may be used to quantitatively or qualitatively detect the presence of cells which express the pcCMT protein. This can be accomplished by immunofluorescence techniques employing a fluorescently labeled antibody (see below) coupled with light microscopic, flow cytometric, or fluorimetric detection.

The biological sample, such as membrane preparation, may be treated with a solid phase support or carrier (which terms are used interchangeably herein) such as nitrocellulose, or other solid support which is capable of immobilizing cells, cell particles or soluble proteins. The support may then be washed with suitable buffers followed by treatment with the detectably labeled pcCMT-specific antibody. The solid phase support may then be washed with the buffer a second time to remove unbound antibody. The amount of bound label on said solid support may then be detected by conventional means.

By "solid phase support or carrier" is intended any support capable of binding antigen or antibodies. Well-known supports, or carriers, include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

The binding activity of a given lot of anti-pcCMT antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the pcCMT-specific antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments, it is possible to detect pcCMT protein through the use of a radioimmunoassay (RIA) (Chard, T., 1978, incorporated by reference herein). The radioactive isotope can be detected by such means as the use of a gamma counter or a liquid scintillation counter or by autoradiography. Radioactively labeled antibodies or antibody fragments can also be used for their capacity to kill cells bound by such antibodies, or cells in the immediate vicinity which are exposed to the radiation from such antibodies.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in an immunometric assay, also known as a "two-site" or "sandwich" assay. In a typical immunometric assay, a quantity of unlabeled antibody (or fragment of antibody) is bound to a solid support and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to "extract" the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

Antibodies or other molecules which include the antigen-binding portion of an antibody may also be used for isolation and purification of pcCMT. Thus, for example, antibodies specific to pcCMT can be immobilized on a solid phase support or carrier with which an impure solution containing pcCMT such as a membrane extract is brought into contact. The pcCMT will bind to the antibodies which are in turn bound to the support while all of the contaminants are washed away. Pure pcCMT can then be eluted from the support by means well-known in the art.

Other utilities will be readily apparent to those of ordinary skill in the art such as, for example, as a tool to assist research into the mechanism of action of the oncogenic ras gene.

Having now generally described the invention, the same will be more readily understood through reference to the following examples which are provided by way of illustration and is not intended to be limiting of the present invention.

EXAMPLE 1

In this example, the present inventors report the molecular characterization and the subcellular localization of the first mammalian (human myeloid) pcCMT. Ectopically expressed recombinant pcCMT were shown to have enzymatic activity identical to that observed in neutrophil membranes. It was unexpectedly discovered by the present inventors that mammalian pcCMT, which is the third of three enzymes that post-translationally modify C-terminal CAAX motifs and thereby target CAAX proteins to the plasma membrane, was not expressed at the plasma membrane but rather restricted to the endoplasmic reticulum. Using pcCMT tagged with green fluorescent protein (GFP), the present inventors have demonstrated below that pcCMT is expressed in the endoplasmic reticulum but excluded from the plasma membrane that is the target of many CAAX proteins, including Ras. Thus, the final enzyme in the sequence of enzymes that modify CAAX motifs is surprisingly located in membranes topologically removed from the CAAX protein target membrane.

The experimental procedures used in this example are as follows:

Northern Blotting: Total RNA (40 μg) from HL60 cells grown with or without 1.25% dimethylsulfoxide (Me$_2$SO) for days was fractionated on a 1.2% denaturing formaldehyde agarose gel, transferred to a nylon filter, and hybridized with [$^{32}$P]dATP-labeled full-length HL60 pcCMT cDNA in Express Hybridization solution (Clontech, Palo Alto, Calif.) at 68° C. A human multiple-tissue Northern blot (Clontech) was hybridized with the same probe according to the manufacturer's instructions. The same filters were stripped and rehybridized with a β-actin probe.

Antiserum: A peptide corresponding to deduced amino acids 185–201 of SEQ ID NO:5 (HL60 pcCMT) was synthesized, inked to keyhole limpet hemocyanin, and used to immunize rabbits. The resulting antiserum was used for immunoblotting of neutrophil light membranes prepared by nitrogen cavitation and discontinuous sucrose density sedimentation (Philips et al, 1991), for immunoprecipitation of lysates of HL60 cells metabolically labeled with L-[$^{35}$S]methionine, and for indirect immunofluorescence of COS-1 cells.

Expression of Recombinant pcCMT: The 3.6-kb full-length HL60 pcCMT cDNA and an 852-bp cDNA fragment comprising the ORF were subcloned into the eukaryotic expression vectors pCDM8 and pcDNA3.1 (Invitrogen, Carlsbad, Calif.). Myc-tagged pcCMT was made by adding a sequence encoding the 10-amino acid epitope of c-Myc recognized by monoclonal antibody 9E10 to the C terminus of pcCMT using patch PCR and subcloning into pcDNA3.1. pcCMT tagged at the C terminus with GFP was generated by subcloning the pcCMT ORF into the expression vector pGFP-N3 (Clontech). For pcCMT enzymatic assays, COS-1 cells were grown in 10-cm dishes and transfected with pcCMT with DEAE-dextran as described (Aruffo et al, 1987). For fluorescence microscopy, exponentially growing COS-1, CHO, and NIH3T3 cells were plated the day prior to transfection at 50–60% confluence and transfected with 2 μg of DNA using LipofectAMINE (Life Technologies, Inc.), Gaithersburg, Md.) according to the manufacturer's instructions. Cells were observed at 24 and 48 hours after transfection.

Prenylcysteine Carboxyl Methyltransferase Assays: COS-1 cells transfected with HL60 pcCMT or vector alone were harvested at 48 hours with 5 mM EDTA and subjected, in parallel with human neutrophils, to nitrogen cavitation and discontinuous sucrose density centrifugation as described (Philips et al, 1991). Light membranes were assayed for pcCMT activity qualitatively by S-adenosyl-L-[methyl-$^3$H]methionine labeling (SDS-polyacrylamide gel electrophoresis and flurography) of Rho GTPases partially purified from neutrophil cytosol and quantitatively by carboxyl methylation of N-acetyl-S-trans,trans-farnesyl-L-cysteine (AFC) (heptane partition, alkaline hydrolysis, and measurement of vapor phase [$^3$H]methanol) as described (Philips et al, 1995)

S. cerevisiae Strains, Growth, and ste14 Complementation: Complete (YEPD), synthetic (SD), and synthetic dropout media were prepared as described previously (Michaelis et al, 1988), except that dropout medium lacked cysteine. All experiments were performed at 30° C. Yeast transformations were carried out by either the lithium acetate method (Ito et al, 1983) or the Elble method (Elble, 1992). The ste14 deletion strains used are SM1188 (MATαΔste14-3:: TRP1 trp1 leu2 ura3 his4 can1) and SM1639 (MATαΔste14-4:: URA3 trp1 leu2 his4 can1) (Sapperstein et al, 1994). Plasmid expression of STE14 protein was accomplished by pSM1237 (CEN URA3 STE14). Human pcCMT was expressed in yeast by subcloning the HL60 pcCMT ORF into the BamHI SalI sites of the yeast expression plasmid pG1 (2μ TRP1) that utilizes a GPD promoter and a PGK transcription terminator and polyadenylation signal (Schena et al, 1991). The resulting construct was designated pG1-hCMT (2μ TRP1 hCMT). Patch mating tests were carried out essentially as described previously (Michaelis et al, 1988). briefly, patches of MATα cells grown on selective media were replica plated onto a lawn of the MATα mating tester, SM1068 (lys1), that had been spread on an SD plate. Plates were incubated at 30° C. for 3 days. Growth of the prototrophic diploids indicated mating.

Fluorescence Microscopy: Live cells that had been transfected with pcCMT-GFP and fixed/permeabilized (2% paraformaldehyde/0.2% Triton X-100 at 4° C. or methanol at −20° C.) cells stained with 9E10 anti-Myc antibody (Santa Cruz Biotechnology, Santa Cruz, Calif.), C6 anti-ribophorin I antiserum (provided by Dr. Gert Kriebich, NYU), or the anti-pcCMT antiserum described above, followed by Texas Red-conjugated secondary antisera, were imaged with a Zeiss Axioscope equipped with a Princeton Instruments cooled CCD camera and a KAF 1400 chip or a Molecular Dynamics confocal microscope equipped with an argon laser.

Cloning of Human Prenylcysteine Carboxyl Methyltransferase (pcCMT)

At the time this work was undertaken, the only S-isoprenylcysteine methyltransferase characterized at the molecular level was the Ste14 gene of S. cerevisiae. Attempts by the laboratory of the present inventor at cloning a homologous gene from human DNA by PCR using degenerate oligonucleotide primers based on the amino acid sequence of STE14 were unsuccessful. Therefore, a search of the GenBank in the Expressed Sequence Tag (EST) Database of the National Center for Biotechnology Information (NCBI) (the website at http://www.2.ncbi.nlm.nih.gov/dbST/dbest_query.html) for mammalian sequences related to Ste14 was performed using the text string "isoprenylcysteine". This search identified a 426 bp partial cDNA as an expressed sequence tag from a murine placental cDNA library (EST name: mh77d06,r1; Genfank Acc: AA022288; GenBank gi: 1486061) that was noted to have amino acid sequence homology to Ste14, The following strategy was then used to generate a eDNA probe with which to screen a human cDNA library for a pcCMT gene.

Membranes prepared from HL60 cells (human promyelocytic leukemia cell line obtained from American Type Culture Collection, Rockville, Md.) have also been reported to express pcCMT enzymatic activity, and, accordingly, total RNA was prepared from HL60 cells and the first strand cDNA was generated with oligo(dt) primers and the reverse transcriptase from Moloney Murine Leukemia Virus. After first strand cDNA synthesis, the original mRNA template was removed by treatment with RNase H, followed by second strand synthesis and PCR amplification of the resultant cDNA was accomplished using Taq DNA polymerase and a pair of primers that were designed based on the EST mh77d06.r1 sequence (forward primer: 5'-GCCGGACTCAACGCGCTGCTGCTGCTACTCTA-3' (SEQ ID NO:1); reverse primer: 5'-CGTGTACTCCAGGCTGTGATTCAGGAGGAA-3' (SEQ ID NO:2)). Thirty-five cycles of PCR were performed using the following conditions: denaturation at 94° C. for 1 minute; annealing at 50° C. for 1 minute; extension at 72° C. for 2 minutes. The PCR products were separated on a 1.5% agarose gel and two bands were observed, the more abundant of which corresponded to a DNA of the predicted size (≈250 bp).

The more abundant PCR reaction product of approximately 250 bp in size was gel purified and sequenced by the dideoxy procedure, and the result revealed a 218 bp sequence (not counting the primers; SEQ ID NO:3) that had high similarity to the murine EST mh77d06.r1 sequence. To subclone this amplified cDNA, the amplification product was purified from the PCR reaction by phenol/chloroform extraction and directly inserted into the pCR™2.1 vector using a TA cloning kit (Invitrogen, San Diego Calif.). $E.$ $coli$ were transformed with the resulting recombinant plasmid and grown to log phase. The plasmid was isolated with a Mini Prep Kit (Qiagen) and the insert was released by EcoRI digestion. The resultant insert, labeled with [$^{32}$P]dATP using a random primer extension labeling system (Ambion, Inc., Austin, Tex.), was used to screen a cDNA library to identify a human pcCMT gene. The screened library was a size-fractionated, unidirectional HL60 cDNA library constructed in the λ lambdaZAP® system (Stratagene, La Jolla, Calif.) and provided by Dr. Philip Murphy of the Laboratory of Host Defenses, National Institute of Allergy and Immunology. Screening was performed in the $E.$ $coli$ strain XL1-blue (Stratagene). An aliquot of the library was plated at a density of 2000 pfu/150-mm petri dish. A total of 20,000 plaques on ten petri dishes were screened. Two duplicate lifts were made from each petri dish, using nitrocellulose membranes.

The lifts were probed with the [$^{32}$P]dATP-labeled 218 bp PCR fragment (SEQ ID NO:3) as described above. Hybridization was performed in 5xSSPE, 1xDenhardt solution, and 0.2% SDS at 56° C. overnight. The filters were washed in 0.2xSSC/0.1% SDS at room temperature for 30 minutes, and 0.1xSSC/0.1% SDS at 55° C. for 40 minutes with two changes and then allowed to dry. Autoradiograms of the filters were analyzed, and plaques were scored as positive only if they appeared on the autoradiograms of duplicate filters. One of the initial 20,000 plaques screened was determined to be positive by this criteria, and a single recombinant phage containing the hybridizing cDNA insert was selected in a secondary screening. Analysis of the recombinant phage revealed a 3.6 kb insert, and sequencing of the insert (SEQ ID NO:4) revealed an open reading frame (nucleotides 44 to 895 of SEQ ID NO:4) that is predicted to direct the synthesis of a 284 amino acid protein having the amino acid sequence of SEQ ID NO:5 (deduced molecular weight of 30 kD) that exhibits 26% identity to the Ste14 gene product. Hydropathy analysis revealed six hydrophobic sequences that may represent membrane-spanning domains (FIG. 3). This is consistent with the five or six putative membrane-spanning domains of STE14 protein (Sapperstein et al, 1994), with recent data demonstrating that STE14 protein is an integral membrane protein (Romano et al, submitted for publication) and with our observation that active pcCMT cannot be extracted from membranes with detergents but can be partially reconstituted in phospholipid vesicles (Pillinger et al, 1994). The first 65 amino acids of human pcCMT, containing the first two hydrophobic sequences, are 36% identical to amino acids 750–821 of the human band 3 anion transporter, which represent the 11th and 12th of 14 well-characterized membrane-spanning domains, further supporting the hypothesis that human pcCMT is a multiple membrane-spanning protein. Comparison of human pcCMT with all related sequences in the GenBank (FIG. 2) revealed the highest degree of divergence in the N-terminal third of the molecule, suggesting that the catalytic domain is C-terminal. Sequences homologous to the S-adenosylmethionine binding regions described in aspartyl and glutamyl protein carboxyl methyltransferase (Volker et al, 1989) were not apparent, arguing against an evolutionary link to these carboxyl methyltransferases.

Further analysis of the cDNA revealed that the initiation codon is flanked by a Kozak consensus sequence, and that no upstream termination codon was found. A polyA sequence 3' to the opening reading frame was found to be present.

Expression of Human Prenylcysteine Carboxyl Methyltransferase

Figure 5A:
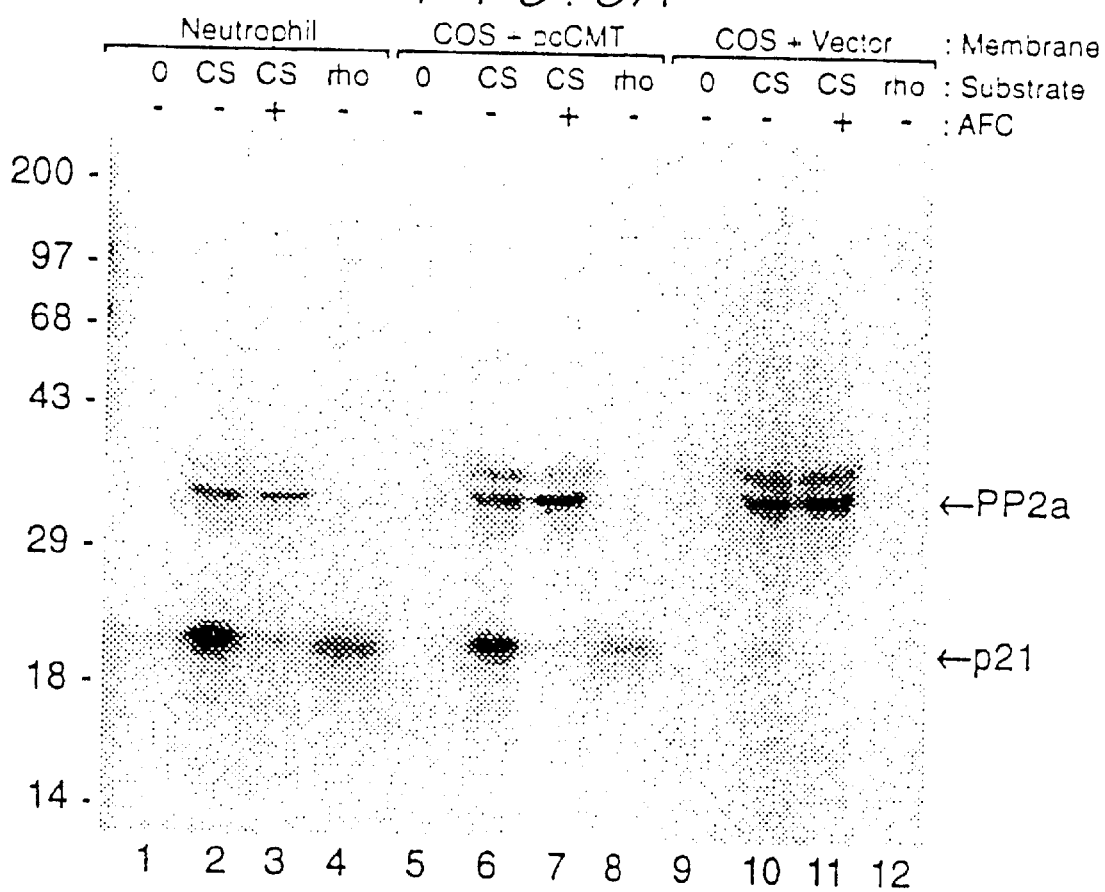
FIGS. 5A and 5B show the carboxyl methylation of ras-related GTPases by COS-1 cell membranes expressing ectopic human pcCMT.
Figure 5B:
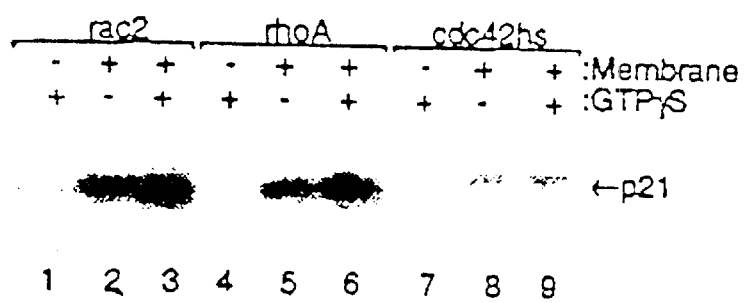

To determine whether the HL60 STE14 protein homolog has prenylcysteine carboxyl methyltransferase activity, the cDNA was subcloned into a mammalian expression vector PCDM8 (Invitrogen, San Diego, Calif.) and transiently overexpressed ectopically in COS-1 cells. Membranes prepared from these cells were used as a source of recombinant enzyme. Farnesylated Ras GTPases require detergent for extraction from membranes. Therefore, geranylgeranylated neutrophil cytosolic Rho accessory protein, guanine nucleotide dissociation inhibitor (GDI), were utilized as endogenous substrates in an in vitro assay (FIGS. 5A and 5B). Untransfected COS-1 cell membranes had little pcCMT activity toward Rho proteins compared with that of membranes derived from human neutrophils (FIG. 5A). Transfection with the HL60 cDNA conferred pcCMT activity toward Rho GTPases on COS-1 membranes, and this activity was blocked by the competitive pcCMT inhibitor, AFC, with an $ED_{50}$ (10 µM) identical to that for endogenous neutrophil pcCMT. Carboxyl methylation of Rac2 and RhoA by HL60 pcCMT-transfected COS-1 cell membranes was enhanced by guanosine 5'-3-O-(thio)triphosphate (GTPγS) (FIG. 5B), similar to the activity observed in neutrophil membranes (Philips et al, 1993). Carboxyl methyltransferase activity was quantitated in membranes of COS-1 cells transfected with HL60 pcCMT using prenylcysteine analogs as defined substrates (Philips et al, 1995). Untransfected COS-1 cell membranes had 23 10% (n=5) of the pcCMT specific activity of neutrophil membranes toward AFC. Transfection of COS-1 cells with HL60 pcCMT resulted in an 18–53-fold increase in specific AFC carboxyl.methyltransferase activity (Table 1; 3.0±0.8 to 74.5±6.8 pmol/mg·min, n=5, p<0.0005).

TABLE 1

Prenylcysteine carboxyl methyltransferase activity in membranes of neutrophils and COS cells ± pcCMT transfection

| Source of Membrane | Experiment 1 | | Experiment 2 | | Experiment 3 | |
|---|---|---|---|---|---|---|
| | Activity pmol/mg/min | Increase (fold) | Activity pmol/mg/min | Increase (fold) | Activity pmol/mg/min | Increase (fold) |
| Neutrophil | 10.3 | 2 | 6.5 | 3.5 | 11.4 | 7 |
| COS + Vector* | 5.3 | 1 | 1.9 | 1 | 1.7 | 1 |
| COS + pcCMT cDNA† | 62.7 | 12 | 17.7 | 9 | 35.3 | 21 |
| COS + pcCMT ORF‡ | ND | ND | 84.6 | 45 | 90.7 | 53 |

*PCDM8;
†pCDM8 + pcCMT full-length cDNA;
‡pCDM8 + pcCMT ORF only.
Transient (48 h) transfections were performed with DEAE-dextran. Membranes were prepared by nitrogen cavitation followed by discontinuous sucrose density centrifugation. Carboxyl methyltransferase activity was determined using AFC as substrate.
Each experiment represents an independent set of transfections.

Carboxyl methylation of N-acetyl-S-all-trans-geranylgeranyl-L-cysteine (AGGC) was increased in parallel with methylation of AFC (18-versus 20-fold increase, n=2), consistent with previous studies demonstrating that a single activity carboxyl methylated both farnesylated and geranylgeranylated substrates (Volker et al, 1991b). The Michaelis constants of the recombinant enzyme, $K_m$=7 $\mu$M for AFC and 0.6 $\mu$M for AGGC, were similar to those for the endogenous neutrophil enzyme (Pillinger et al, 1994). Thus, the cDNA described above encodes authentic human myeloid pcCMT.

To determine whether human pcCMT could substitute in vivo for the S. cerevisiae pcCMT, STE14 protein, a complementation analysis was done using mating as a biological readout. The HL60 pcCMT cDNA expressed from a plasmid in a Δste14 yeast strain partially restored the mating phenotype, indicating that a factor could be carboxyl methylated by human pcCMT. Thus, HL60 pcCMT is a functional human homolog of S. cerevisiae STE14 protein.

Figure 6A:
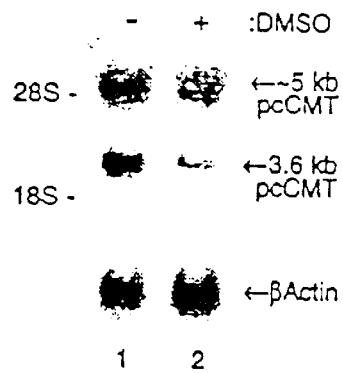
FIGS. 6A and 6B show Northern analysis of human tissues for expression of pcCMT mRNA and FIG. 6C shows immunoblot analysis of expressed pcCMT protein.
Figure 6B:
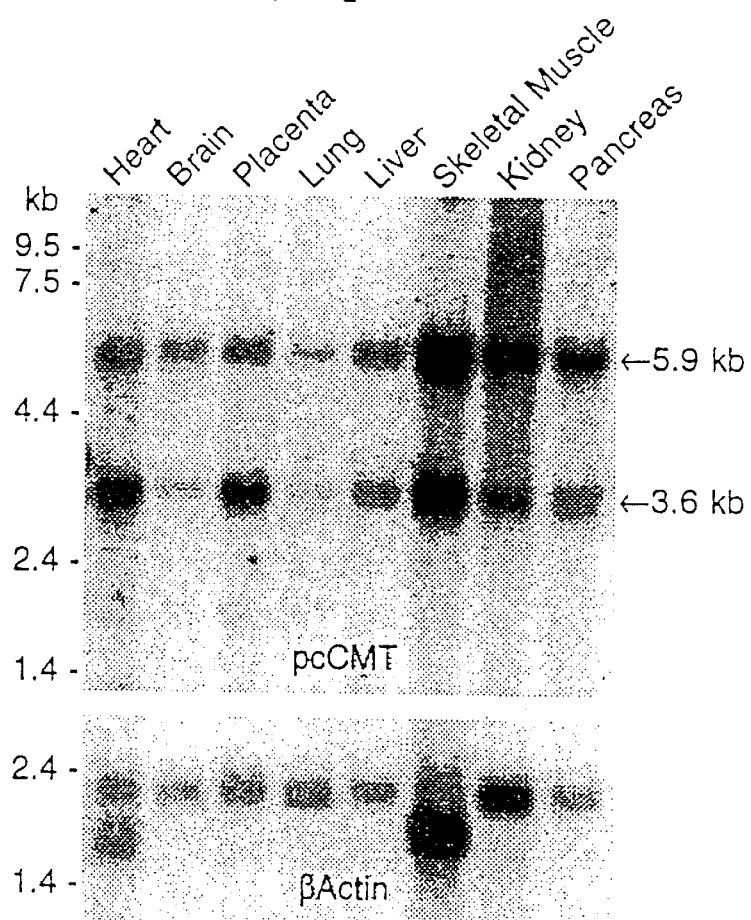

Expression of the human pcCMT gene was examined by Northern analysis. HL60 cells expressed two pcCMT mRNAs, a 3.6-kb transcript consistent with the isolated cDNA and a 5-kb transcript suggesting a related gene or an alternatively spliced message (FIG. 6A). The level of expression of both transcripts was diminished by granulocytic differentiation of HL60 cells induced by Me$_2$SO, consistent with our observation that HL60 membranes have 5-fold greater specific pcCMT activity than membranes of mature, peripheral blood neutrophils. Both transcripts were ubiquitously expressed in human tissues (FIG. 6B).

Figure 6C:
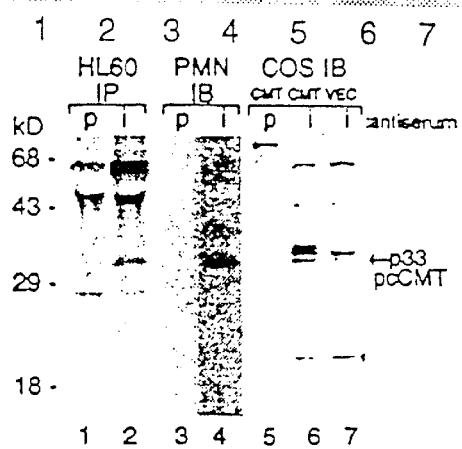

To characterize endogenous pcCMT, a polyclonal antiserum was raised against an internal HL60 pcCMT peptide (amino acids 184–201 of SEQ ID NO:5). Immunoblots of neutrophil and pcCMT-transfected COS-1 cell membranes using this antiserum revealed a 33-kDa protein (FIG. 6C) corresponding to the predicted size of the protein encoded by the HL60 pcCMT cDNA, confirming that this cDNA, which lacked a termination codon 5' of the ORF is, in fact, full-length. The same antiserum immunoprecipitated a 33-kDa protein from HL60 cells (FIG. 6C). Although the deduced amino acid sequence of pcCMT reveals a potential N-glycosylation site (FIG. 2), these data argue against glycosylation.

To tag pcCMT for both the study of the biology of pcCMT and the isolation of the enzyme, sequences encoding C-terminal epitope tags (Myc, FLAG, and GFP) were added to the 3'-end of the pcCMT gene as a C-terminal extension. Myc is a widely-used 10-amino acid epitope recognized by the very efficient, commercially available 9E10 monoclonal antibody, and FLAG is an 8-amino acid epitope efficiently recognized by a proprietary monoclonal antibody commercially available from Eastman Kodak. Green fluorescent protein (GFP) is a 27 kDa protein derived from a jellyfish that is intrinsically fluorescent and, therefore, can tag molecules with a fluorescent epitope that can be visualized in living cells. Table 2 presents the results obtained on the effect of these C-terminal epitope tags on relative enzymatic activity of human pcCMT ectopically expressed in COS cell membranes. Neither the Myc nor FLAG epitopes as C-terminal extensions of pcCMT affect its carboxyl methyltransferase activity when ectopically expressed in COS cell membranes. This shows that epitope tagged pcCMT can be easily quantitated in cells by immunochemical techniques and the isolation of the enzyme is facilitated because Myc- or FLAG-tagged pcCMT could be easily affinity purified and then enzymatically reconstituted in liposomes to provide a biochemically defined target for screening potential pcCMT inhibitors. The data on GFP-tagged CMT are inconclusive and will be repeated.

TABLE 2

Effect of C-Terminal Epitope Tags (Myc, FLAG, and GFP) on Relative Enzymatic Activity of Human pcCMT Ectopically Expressed in Cos Cell Membranes

| Construct | Experiment | | |
|---|---|---|---|
| | #1 | #2 | #3 |
| Vector Alone | 1 | 1 | 1 |
| pcCMT | 14.1 | 5.4 | 19.6 |
| PcCMT-Myc | 11.1 | | |
| pcCMT-FLAG | | 5.45 | 18.5 |
| pcCMT-GFP | 2.1 | | |

Ras is constitutively carboxyl methylated (Clarke et al, 1988) and expressed at the plasma membrane (Willingham et al, 1980), a localization required for its biological activity (Willingham et al, 1980). Like all CAAX proteins, Ras lacks a signal peptide, is synthesized in the cytosol, and modified immediately posttranslationally by a cytosolic prenyltransferase (Casey et al, 1996). Because prenylcysteine carboxyl methylation is catalyzed by an intrinsic membrane protein and represents the last of the three posttranslational modifications of the CAAX cysteine that enhance the affinity of Ras for membranes, the simplest model of plasma membrane targeting predicts pcCMT expression in the target membrane. However, activities associated with the further processing of prenylated proteins, including pcCMT (Stephenson et al, 1992), S-isoprenyl-CAAX high affinity binding (Thissen et al, 1993), S-isoprenyl-CAAX protease (Hancock et al, 1991; Ma et al, 1992), and palmitoyltransferase (Kasinathan et al, 1990) activities, have all been reported in microsomal fractions. Furthermore, one of the two S-isoprenyl-CAAX proteases recently identified in yeast has a putative ER retention sequence (Boyartchuk et al, 1997; Fujimura-Kamada et al, 1997), and a double deletion of these genes led to mislocalization of yeast Ras2p to internal membranes and cytosol (Boyartchuk et al, 1997). Nevertheless, none of these studies excluded expression of prenylcysteine-modifying activities from plasma membranes. Indeed, the present inventors have reported pcCMT activity in neutrophil subcellular fractions enriched for surface membrane (Pillinger et al, 1994).

Figure 7A:
FIGS. 7A–7I show the subcellular localization of human pcCMT.
Figure 7B:
Figure 7C:
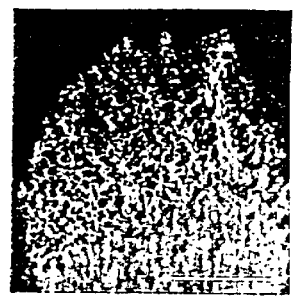
Figure 7D:
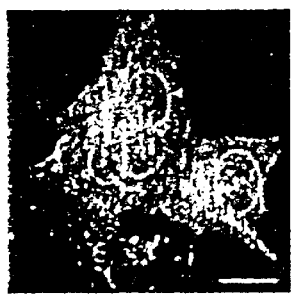
Figure 7E:
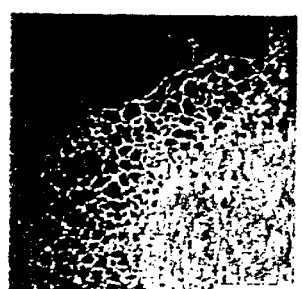
Figure 7F:
Figure 7G:
Figure 7H:
Figure 7I:
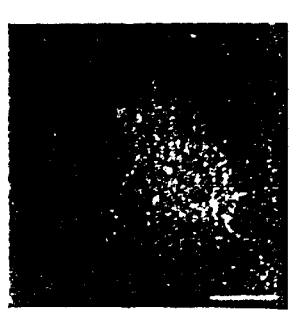

To determine the subcellular localization of pcCMT, a recombinant pcCMT tagged at the C terminus with GFP was constructed. In CHO (FIGS. 7A–7C), COS-1 (FIGS. 7D and 7E), and HIH3T3 (not shown) cells, CMT-GFP was visualized in the ER, Golgi, and nuclear membranes but not in the plasma membrane. This assay afforded a sensitivity and resolution that allowed visualization of individual ER canaliculi extending to the periphery of the cell (FIGS. 7C and 7D) and was, therefore, definitive in excluding expression in the plasma membrane. ER expression was confirmed by colocalization with the ER marker ribophorin I (FIG. 7F), a component of the glycosyltransferase complex restricted to ER. Because the 27-kDa GFP added to the C terminus of pcCMT might alter its native subcellular localization, the CMT-GFP localization was confirmed with a pcCMT tagged at the C terminus with a 10-amino acid Myc epitope (FIG. 7G). Finally, an anti-peptide antiserum reactive with pcCMT was used to confirm these data by localizing endogenous pcCMT to ER and nuclear membranes in COS-1 cells (FIGS. 7H and 7I). The absence of Golgi staining for endogenous pcCMT suggests that the Golgi localization of ectopically expressed pcCMT may result from gene overexpression.

These data demonstrate that mammalian pcCMT is an intrinsic membrane protein localized to a compartment topologically removed from the plasma membrane, and show that Ras-related, GTPases and $G_y$, that are targeted to the cytoplasmic face of the plasma membrane where they participate in signaling events, complete their posttranslational processing in the ER.

Figure 8C:
FIGS. 8A–8C show the effect of a pcCMT inhibitor (AFC) on the subcellular localization of Nras.
Figure 8B:
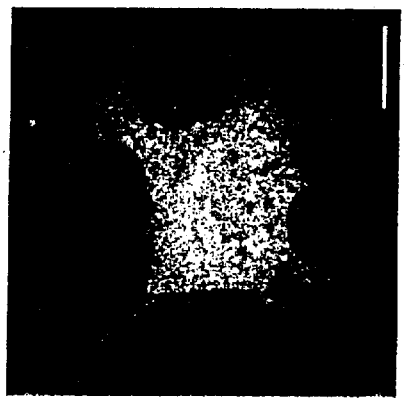
Figure 8A:
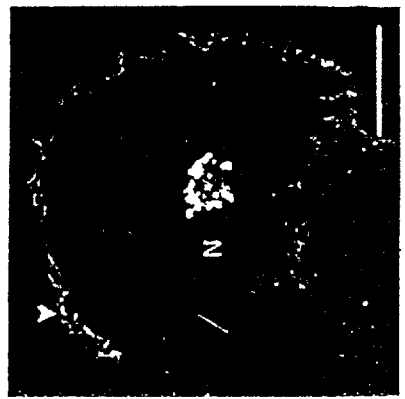

In order to determine the role of carboxyl methylation on membrane targeting of Ras, Ras molecules tagged at their N-termini with the intrinsically fluorescent protein, green fluorescent protein (GFP) was constructed. As predicted, GFP-Nras was localized in the plasma membrane (FIG. 8A). Somewhat surprising was the localization of GFP-Nras in the membrane of the Golgi as well. In contrast, when a Ras mutant with an altered CAAX motif that cannot be farnesylated (NrasC186S) was tagged with GFP, all of the GFP-Nras remained in the cytosol (FIG. 8B), confirming that farnesylation is required for plasma membrane localization. Farnesyltransferase inhibitors would, therefore, be expected to result in the retention of GFP-Nras in the cytosol. When a carboxyl methyltransferase inhibitor, AFC, was applied to this system, the proper membrane localization of GFP-Nras was blocked and most of the molecules remained cytosolic (FIG. 8C), similar to the GFP-Nras blocked at the level of farnesylation. Since farnesylation and carboxyl methylation are distinct steps in a sequential biochemical process, inhibitors of these enzymes would be expected to have synergistic effects.

It is surprising that proteins, such as Ras, synthesized on free ribosomes, prenylated in the cytosol, and destined form the cytoplasmic leaflet of the plasma membrane, are diverted to the ER for processing. Moreover, the ER restriction of pcCMT suggests that an uncharacterized transport pathway must mediate the translocation of fully processed GTPases from internal membranes to the cell surface. Such a pathway could utilize the cytoplasmic surface of secretory vesicles, cytosolic accessory molecules analogous to GDI, or a novel transport system.

EXAMPLE 2
Carboxyl Methyltransferase Assay Using Streptavidin-bound Biotinylated Substrate In a 96 multiwell format, the assay has a capacity for testing five compounds in quadruplicates, with controls, as inhibitors of pcCMT activity. For a 100 μl final assay volume, a mixture of a prenylated (farnesylated or geranylgeranylated) peptide substrate (approx. 2 μmols of a GlyGlyTyrGlnLysArgAlaCys (SEQ ID NO:13) peptide), which is also biotinylated at its N-terminus, is mixed with a solution of the test compound. A 45 μl volume of this mixture is transferred to each well in a 96 well REACTI-BIND plate (Pierce) and to which a 40 μl/well mixture of S-adenosyl-L-[$^3$H]-methionine (1 uCi/10 μl of specific activity 56.1 Ci/mmol) with 3.6 ml of a membrane preparation containing pcCMT activity. The complete reaction mixture is then incubated at 37□C for one hour. After washing with a wash buffer, 100 μl of WALLAC OY scintillation fluid (Wallac) is added to all wells and allowed to stand for 45–60 minutes before transferring the scintillation fluid from all the wells into a WALLAC OY plate to measure counts per minute (cpm).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Akasako et al, "High resistance of *Escherichia coli* ribonuclease HI variant with quintuple thermostabilizing mutations to thermal denaturation, acid denaturation, and proteolytic degradation", *Biochemistry* 34(25):8115–8122 (1995)

Alber et al, "Temperature-sensitive mutations of bacteriophage T4 lysozyme occur at sites with low mobility and low solvent accessibility in the folded protein", *Biochemistry* 26(13):3751–3758 (1987)

Allen et al, "Identification of the T-cell and Ia contact residues of a T-cell antigenic epitope", *Nature* 327(6124):713 (1987)

Altschuh et al, "Coordinated amino acid changes in homologous protein families", *Protein Eng.* 2(3):193–199 (1988)

Aruffo et al, "Molecular cloning of a CD28 cDNA by a high-efficiency COS cell expression system", *Proc. Natl. Acad. Sci. USA* 84(23):8573–8577 (1987)

Ashby et al, "Isolation and DNA sequence of the STE14 gene encoding farnesyl cysteine: carboxyl methyltransferase", *Yeast* 9(8):907–913 (1993)

Ausubel et al (Eds), *Current Protocols in Molecular Biology*, Greene Publications and Wiley Interscience (New York, N.Y., 1987–1997)

Ballinger et al, "Designing subtilisin BPN' to cleave substrates containing dibasic residues", *Biochemistry* 34(41):13312–13319 (1995)

Barbacid, "ras genes", *Ann. Rev. Biochem.* 56:779–827 (1987)

Behravan et al, "Structural and functional differences between carbonic anhydrase isoenzymes I and II as studied by site-directed mutagenesis", *Eur. J. Biochem.* 198(3):589–592 (1991)

Better et al, "*Escherichia coli* secretion of an active chimeric antibody fragment", *Science* 240(4855):1041–1043 (1988)

Blacklow et al, "Stepwise improvements in catalytic effectiveness: independence and interdependence in combinations of point mutations of a sluggish triosephosphate isomerase", *Biochemistry* 30(34):8470–8476 (1991)

Boulianne et al, "Production of functional chimaeric mouse/human antibody", *Nature* 312(5995):643–646 (1984)

Boyartchuk et al, "Modulation of Ras and a-factor function by carboxyl-terminal proteolysis", *Science* 275(5307):1796–1800 (1997)

Cabilly et al, "Generation of antibody activity from immunoglobulin polypeptide chains produced in *Escherichia coli*", *Proc. Natl. Acad. Sci. USA* 81(11):3273–3277 (1984)

Casey et al, "Protein prenyltransferases", *J. Biol. Chem.* 271(10):5289–5292 (1996)

Chard (In: Work et al, *Laboratory Techniques in Biochemistry in Molecular Biology*, North Holland Publishing Company (New York 1978)

Chelsky et al, "Methyl-esterified proteins in a mammalian cell line", *Biochemistry* 24(23):6651 (1985)

Claessens et al, "Modelling the polypeptide backbone with 'spare parts' from known protein structures", *Protein Eng.* 2(5):335–345 (1989)

Clarke et al, "Posttranslational modification of the Ha-ras oncogene protein: evidence for a third class of protein carboxyl methyltransferases", *Proc. Natl. Acad. Sci. USA* 85(13):4643–4647 (1988)

Clarke, "Protein isoprenylation and methylation at carboxyl-terminal cysteine residues", *Ann. Rev. Biochem.* 61:355–386 (1992)

Colligan et al (Eds), *Current Protocols in Immunology*, Green Publishing Assoc., and Wiley Interscience (New York, 1993)

Constantino et al, "Homology modeling of metabotropic glutamate receptors. (mGluRs) structural motifs affecting binding modes and pharmacological profile of mGluR1 agonists and competitive antagonists", *J. Med. Chem.* 39(20):3998–4006 (1996)

Darnell et al, *Molecular Cell Biology*, Scientific American Books, Inc., (New York, N.Y., 1986)

Elble, "A simple and efficient procedure for transformation of yeasts", *Biotechniques* 13(1):18–20 (1992)

Eshhar et al, "Chimeric T cell receptor which incorporates the anti-tumour specificity of a monoclonal antibody with the cytolytic activity of T cells: a model system for immunotherapeutical approach", *Br. J. Cancer Suppl.*, 10:27–29 (1990)

Finegold et al, "Protein geranylgeranyltransferase of *Saccharomyces cerevisiae* is specific for Cys-Xaa-Xaa-Leu motif proteins and requires the CDC43 gene product but not the DPR1 gene product", *Proc. Natl. Acad. Sci. USA* 88(10):4448 (1991)

Fujimura-Kamada et al, "A novel membrane-associated metalloprotease, Ste24p, is required for the first step of NH2-terminal processing of the yeast a-factor precursor", *J. Cell Biol.* 136(2):271–285 (1997)

Gibbs, "Ras C-terminal processing enzymes—new drug targets?", *Cell* 65(1):1–4 (1991)

Gibbs et al, "Farnesyltransferase inhibitors and anti-Ras therapy", *Breast Cancer Res. and Treatment* 38(1):75–83 (1996)

Glomset et al, "Prenyl proteins in eukaryotic cells: a new type of membrane anchor", *Trends Biochem. Sci.* 15(4):139–142 (1990)

Gloss et al, "Contribution to catalysis and stability of the five cysteines in *Escherichia coli* aspartate aminotransferase. Preparation and properties of a cysteine-free enzyme", *Biochemistry* 31(1):32–39 (1992)

Green et al, "Patterns of nonadditivity between pairs of stability mutations in staphylococcal nuclease", *Biochemistry* 32(38):10131–10139 (1993)

Gregoret et al, "Additivity of mutant effects assessed by binomial mutagenesis", *Proc. Nat. Acad. Sci. USA* 90(9):4246–4250 (1993)

Gross et al, "Expression of immunoglobulin-T-cell receptor chimeric molecules as functional receptors with antibody-type specificity", *Proc. Natl. Acad. Sci. USA* 86(24):10024–10028 (1989)

Guruprasad et al, "Comparative modelling and analysis of amino acid substitutions suggests that the family of pregnancy-associated glycoproteins includes both active and inactive aspartic proteinases", *Protein Eng.* 9:849–856 (1996)

Guyer et al, Cloning, sequencing, and expression of the gene encoding the porcine alpha 2-adrenergic receptor. Allosteric modulation by Na+, H+, and amiloride analogs *J. Biol. Chem.* 265(28):17307–17317 (1990)

Hancock et al, "A polybasic domain or palmitoylation is required in addition to the CAAX motif to localize p21ras to the plasma membrane", Cell 63(1):133–139 (1990)

Hancock et al, "Methylation and proteolysis are essential for efficient membrane binding of prenylated p21K-ras(B)", EMBO J. 10(3):641–646 (1991)

Harlow et al, Antibodies: A Laboratory Manual, Cold Spring Harbor Laboratory (1988)

Hrycyna et al, "Farnesyl cysteine C-terminal methyltransferase activity is dependent upon the STE14 gene product in Saccharomyces cerevisiae", Mol. Cell. Biol. 10(10):5071–5076 (1990)

Hrycyna et al, "The Saccharomyces cerevisiae STE14 gene encodes a methyltransferase that mediates C-terminal methylation of a-factor and RAS proteins", EMBO J. 10(7):1699–1709 (1991)

Huzoor-Akbar et al, "Protein prenylcysteine analog inhibits agonist-receptor-mediated signal transduction in human platelets", Proc. Natl. Acad. Sci. USA 90(3):868–872 (1993)

Imai et al, "Genes encoding farnesyl cysteine carboxyl methyltransferase in Schizosaccharomyces pombe and Xenopus laevis", Mol. Cell. Biol. 17(3):1543–1551 (1997)

Ingrosso et al, "Sequence of the D-aspartyl/L-isoaspartyl protein methyltransferase from human erythrocytes. Common sequence motifs for protein, DNA, RNA, and small molecule S-adenosylmethionine-dependent methyltransferases", J Biol Chem 264(33):20131–20139 (1989)

Ito et al, "Carbonyl cyanide-m-chlorophenyl hydrazone-resistant Escherichia coli mutant that exhibits a temperature-sensitive unc phenotype", J Bacteriol 153(1):163–168 (1983)

Jenkins et al, "Structure and chromosomal location of the human gene encoding cartilage matrix protein", J Biol Chem 265(32):19624–19631 (1990)

Jameson et al, "The antigenic index: a novel algorithm for predicting antigenic determinants", Comput Appl Biosci 4(1):181–186 (1988)

Johnson et al, "Knowledge-based protein modeling", Crit Rev Biochem & Mol Biol 29(1):1–68 (1994)

Jones et al, Curr Comm Molec Biol 1986

Kasinathan et al, "Purification of protein fatty acyltransferase and determination of its distribution and topology", J Biol Chem 265(9):5139–5144 (1990)

Kelly et al, "Thermodyamic analysis of an antibody functional epitope", Biochemistry 32(27):6828–6835 (1993)

Kinsella et al, "rab GTP-binding proteins with three different carboxyl-terminal cysteine motifs are modified in vivo by 20-carbon isoprenoids", J Biol Chem 267(6):3940–3945 (1992)

Koblan et al, "Farnesyltransferase inhibitors: a new class of cancer chemotherapeutics", Biochem Soc Transactions 24(3):688–692 (1996)

Kohler et al, "Continuous cultures of fused cells secreting antibody of predefined specificity", Nature 256 (5517):495–497 (1975)

Lee et al, "Protein phosphatase 2A catalytic subunit is methyl-esterified at its carboxyl terminus by a novel methyltransferase", 5 J Biol Chem 268(26):19192–19195 (1993)

Lewin, Genes II, John Wiley & Sons (New York, N.Y., 1985)

LiCata et al, "Long-range, small magnitude nonadditivity of mutational effects in proteins", Biochemistry 34(10):3133–3139 (1995)

Lim et al, "Alternative packing arrangements in the hydrophobic core of lambda repressor", Nature 339(6219):31–36 (1989)

Lim et al, "Structural and energetic consequences of disruptive mutations in a protein core", Biochemistry 31(17):4324–4333 (1992)

Lin et al, "Specific alteration of the oxidation potential of the electron donor in reaction centers from Rhodobacter sphaeroides", Proc Natl Acad Sci USA 91(22):10265–10269 (1994)

Liu et al, "Chimeric mouse-human IgG1 antibody that can mediate lysis of cancer cells", Proc Natl Acad Sci USA 84(10):3439–3443 (1987)

Lowman et al, "Exchanging interleukin-8 and melanoma growth-stimulating activity receptor binding specificities", J Biol Chem, 266(24):10982–8 (1991)

Lowman et al, "Affinity maturation of human growth hormone by monovalent phage display" J Mol Biol 234(3):564–578 (1993)

Ma et al, "A microsomal endoprotease that specifically cleaves isoprenylated peptides", Proc Natl Acad Sci USA 89(14):6275–6279 (1992)

Maltese, W. "Posttranslational modification of proteins by isoprenoids in mammalian cells", FASEB J 4(15):3319–3328 (1990)

Marcus et al, "Significance of C-terminal cysteine modifications to the biological activity of the Saccharomyces cerevisiae a-factor mating pheromone", Mol Cell Biol 11(7):3603–3612 (1991)

Messing et al, Third Cleveland Symposium on Macromolecules and Recombinant DNA, Editor A. Walton, Elsevier, Amsterdam (1981)

Michaelis et al, "The a-factor pheromone of Saccharomyces cerevisiae is essential for mating", Mol Cell Biol 8(3):1309–1318 (1988)

Morrison et al, "Chimeric human antibody molecules: mouse antigen-binding domains with human constant region domains", Proc Natl Acad Sci USA 81(21):6851–6855, 1984

Murata et al, Molecular cloning and expression of the human interleukin 5 receptor", J Exp Med 175(2):341–351 (1992)

Neuberger et al, "A hapten-specific chimaeric IgE antibody with human physiological effector function", Nature 314 (6008):268–270, 1985

Okayama et al, "A cDNA cloning vector that permits expression of cDNA inserts in mammalian cells", Mol Cell Biol 3(2):280 (1983)

Old et al, Principles of Gene Manipulation: An Introduction to Genetic Engineering, 2d edition, University of California Press (Berkeley, Calif., 1981)

Oliff et al, "New Molecular Targets for Cancer Therapy", Sci Am 275(3):144–149 (1996)

Overington et al, "Environment-specific amino acid substitution tables: tertiary templates and prediction of protein folds", Protein Science 1(2):216–226 (1992)

Paris et al, "Isoprenylation/methylation of proteins enhances membrane association by a hydrophobic mechanism", Biochemistry 35(26):8473–8477 (1996)

Philips et al, "Low molecular weight GTP-binding proteins in human neutrophil granule membranes", J Biol Chem 266(2) :1289–1298 (1991)

Philips et al, "Carboxyl methylation of Ras-related proteins during signal transduction in neutrophils", Science 259 (5097):977–980 (1993)

Philips et al, "Activation-dependent carboxyl methylation of neutrophil G-protein gamma subunit", Proc Natl Acad Sci USA 92(6):2283–2287 (1995a)

Philips et al, "Prenylcysteine-directed carboxyl methyltransferase activity in human neutrophil membranes", Meth Enzymol 256:49–63 (1995b)

Pillinger et al, "Characterization of a plasma membrane-associated prenylcysteine-directed alpha carboxyl methyltransferase in human neutrophils", *J Biol Chem* 269:1486–1492 (1994)

Rodenhuis, S., "ras and human tumors" *Semin Cancer Biol* 3(4):241–247 (1992)

Ruf et al, "Factor VIIa residue Arg290 is required for efficient activation of the macromolecular substrate factor X", *Biochemistry* 33(38):1565–1572 (1994)

Sahagan et al, "A genetically engineered murine/human chimeric antibody retains specificity for human tumor-associated antigen", *J Immunol* 137(4):1066–1074 (1986)

Sambrook et al, *Molecular Cloning: A Laboratory Manual*, Cold Spring Harbor Laboratory (Cold Spring Harbor, N.Y., 1989)

Sandberg et al, "Engineering multiple properties of a protein by combinatorial mutagenesis", *Proc Nat. Acad Sci USA* 90(18):8367–83 (1993)

Sapperstein et al, "Nucleotide sequence of the yeast STE14 gene, which encodes farnesylcysteine carboxyl methyltransferase, and demonstration of its essential role in a-factor export", *Mol Cell Biol* 14(2):1438–1449

Schena et al, "Vectors for constitutive and inducible gene expression in yeast", *Methods Enzymol* 194:389–398 (1991)

Schreiber et al, "Energetics of protein-protein interactions: analysis of the barnase-barstar interface by single mutations and double mutant cycles", *J Mol Biol* 248(2):478–486 (1995)

Schwinn et al, "Molecular cloning and expression of the cDNA for a novel alpha 1-adrenergic receptor subtype", *J Biol Chem* 265(14):8183–81 (1990)

Seabra, et al,"Protein farnesyltransferase and geranylgeranyltransferase share a common alpha subunit", *Cell* 65(3):429–434 (1991)

Shi et al, "Kinetic mechanism of isoprenylated protein methyltransferase", *J Biol Chem* 267(14):9547–9551 (1992)

Silvius et al, "Fluorimetric evaluation of the affinities of isoprenylated peptides for lipid bilayers", *Biochemistry* 33(10):3014–3022 (1994)

Sprague, Jr., "Assay of yeast mating reaction", *Methods Enzymol* 194:77–93 (1991)

Stephenson et al, "Identification of a C-terminal protein carboxyl methyltransferase in rat liver membranes utilizing a synthetic farnesyl cysteine-containing peptide substrate", *J Biol Chem* 265(27):16248–16254 (1990)

Stephenson et al, "Characterization of a rat liver protein carboxyl methyltransferase involved in the maturation of proteins with the -CXXX C-terminal sequence motif", *J Biol Chem* 267(19):13314–13319 (1992)

Stock et al, "Bacterial chemotaxis and the molecular logic of intracellular signal transduction networks", *Ann Rev Biophys Biophys Chem* 20:109–136 (1991)

Sun et al, "Chimeric antibody with human constant regions and mouse variable regions directed against carcinoma-associated antigen 17-1A", *Proc Natl Acad Sci USA* 84(1):214–218 (1987)

Thissen et al, "Microsomal membranes contain a high affinity binding site for prenylated peptides", *J Biol Chem* 268(19):13780–13783 (1993)

Unger et al, "A 3D building blocks approach to analyzing and predicting structure of proteins" *Proteins* 5(4):355–373 (1989)

Vieira et al, "Production of single-stranded plasmid DNA", *Meth Enzymol* 153:3–11 (1987)

Venkatachalam et al, "Characterization of TEM-1 beta-lactamase mutants from positions 238 to 241 with increased catalytic efficiency for ceftazidime", *J Biol Chem* 269(38):23444–23450 (1994)

Venkatasubramanian et al,"Protein methylesterase and leukocyte chemotaxis", *Mol Immunol* 17(2):201–207 (1980)

Volker et al, "Effects of farnesylcysteine analogs on protein carboxyl methylation and signal transduction", *J Biol Chem* 266(32):21515–21522 (1991a)

Volker et al, "A single activity carboxyl methylates both farnesyl and geranylgeranyl cysteine residues", *FEBS Lett* 295(1–3):189–194 (1991b)

Volker et al, "Prenylcysteine analogs to study function of carboxylmethylation in signal transduction" *Meth Enzymol* 250:216–225 (1995)

Wahl et al, "Improved radioimaging and tumor localization with monoclonal F(ab')2", *J Nucl Med* 24(4):316–325 (1983)

Watanabe et al, "Multiple proline substitutions cumulatively thermostabilize *Bacillus cereus* ATCC7064 oligo-1,6-glucosidase. Irrefragable proof supporting the proline rule", *Eur J Biochem* 226(2):277–283 (1994)

Watson et al, *Molecular Biology of the Gene,* Vols I and II, The Benjamin/Cummings Publishing Company, Inc., (Menlo Park, Calif., 1987)

Wells, J., "Additivity of mutational effects in proteins", *Biochemistry* 29(37):8509–8517 (1990)

Williams et al, "Mapping of an NH2-terminal ligand binding site of the insulin receptor by alanine scanning mutagenesis", *J Biol Chem* 270(7):3012–3016 (1995)

Willingham et al, "Localization of the src gene product of the Harvey strain of MSV to plasma membrane of transformed cells by electron microscopic immunocytochemistry", *Cell* 19(4):1005–1014 (1980)

Willumsen et al, "Harvey murine sarcoma virus p21 ras protein: biological and biochemical significance of the cysteine nearest the carboxy terminus", *EMBO J* 3(11):2581–2585 (1984)

Yu et al, "Contribution of individual side-chains to the stability of BPTI examined by alanine-scanning mutagenesis", *J Mol Biol* 249(2):388–397 (1995)

Zuckermann et al, "dentification of highest-affinity ligands by affinity selection from equimolar peptide mixtures generated by robotic synthesis", *Proc Natl Acad Sci USA* 89(10):4505–4509 (1992)

What is claimed is:

1. An isolated antibody or antigen-binding fragment thereof which binds to an epitope of the protein consisting of the amino acid sequence of SEQ ID NO:5.

2. The antibody or antigen-binding fragment thereof in accordance with claim 1, wherein said antibody is a polyclonal antibody.

3. The antibody or antigen-binding fragment thereof in accordance with claim 1, wherein said antibody is a monoclonal antibody.

4. The antibody or antigen binding fragment thereof in accordance with claim 1, wherein said antigen binding fragment is the Fab fragment, the Fab' fragment, the F(ab')$_2$ fragment or the variable portion of the heavy and/or light chain of said antibody.

5. The antibody or antigen binding fragment thereof in accordance with claim 1, wherein the antibody is a chimeric antibody or a single chain antibody.

6. A molecule for delivery of a therapeutic or detectable moiety to a protein consisting of the amino acid sequence of SEQ ID NO:5, said molecule consisting essentially of a therapeutic or detectable moiety and an antibody, or an antigen-binding portion thereof, specific for an epitope of the protein consisting of the amino acid sequence of SEQ ID NO:5.

7. A molecule consisting essentially of a chimeric T cell receptor bearing an antigen-binding portion of an antibody specific for an epitope of the protein consisting of the amino acid sequence of SEQ ID NO:5.

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 1:

```
GCCCGACTCA ACGCGCTGCT GCTGCTACTC TA                              32
```

(2) INFORMATION FOR SEQ ID NO: 2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

```
CGTGTACTCC AGGCTGTGAT TCAGGAGGAA                                 30
```

(2) INFORMATION FOR SEQ ID NO: 3:

(i) SEQUENCE CHARACTERISTICS:
        (A) LENGTH: 218 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
CGGCCGCCTC GCTACCAGAT AGCCATCCGA GCTTGTTTCC TGGGGTTTGT GTTCGGCTGC   60

GGCACGCTGC TAAGTTTTAG CCAGTCTTCT TGGAGTCACT TTGGCTGGTA CATGTGCTC   120

CTGTCATTGT TCCACTATTC TGAATACTTG GTGACAGCAG TCAATAATCC CAAAAGTCT   180

TCCTTGGATT CCTTCCTCCT GAATCACAGC CTGGAGTA                         218
```

(2) INFORMATION FOR SEQ ID NO: 4:

(i) SEQUENCE CHARACTERISTICS:
        (A) LENGTH: 3597 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 44..895

(xi) SEQUENCE DESCRIPTION: SEQ ID NO: 4:

```
GGCACGAGCG GCGCCGCCGC CCGCTAGTCC GCCGCCCGGC GCC ATG GCG GGC TGC     55
                                             Met Ala Gly Cys
                                              1

GCG GCG CGG GCT CCG CCG GGC TCT GAG GCG CGT CTC AGC CTC GCC ACC    103
Ala Ala Arg Ala Pro Pro Gly Ser Glu Ala Arg Leu Ser Leu Ala Thr
 5                  10                  15                  20

TTC CTG CTG GGC GCC TCG GTG CTC GCG CTG CCG CTG CTC ACG CGC GCC    151
Phe Leu Leu Gly Ala Ser Val Leu Ala Leu Pro Leu Leu Thr Arg Ala
            25                  30                  35
```

```
GGC CTG CAG GGC CGC ACC GGG CTG GCG CTC TAC GTG GCC GGG CTC AAC        199
Gly Leu Gln Gly Arg Thr Gly Leu Ala Leu Tyr Val Ala Gly Leu Asn
             40                  45                  50

GCG CTG CTG CTG CTG CTC TAT CGG CCG CCT CGC TAC CAG ATA GCC ATC        247
Ala Leu Leu Leu Leu Leu Tyr Arg Pro Pro Arg Tyr Gln Ile Ala Ile
         55                  60                  65

CGA GCT TGT TTC CTG GGG TTT GTG TTC GGC TGC GGC ACG CTG CTA AGT        295
Arg Ala Cys Phe Leu Gly Phe Val Phe Gly Cys Gly Thr Leu Leu Ser
 70                  75                  80

TTT AGC CAG TCT TCT TGG AGT CAC TTT GGC TGG TAC ATG TGC TCC CTG        343
Phe Ser Gln Ser Ser Trp Ser His Phe Gly Trp Tyr Met Cys Ser Leu
 85                  90                  95                 100

TCA TTG TTC CAC TAT TCT GAA TAC TTG GTG ACA GCA GTC AAT AAT CCC        391
Ser Leu Phe His Tyr Ser Glu Tyr Leu Val Thr Ala Val Asn Asn Pro
                105                 110                 115

AAA AGT CTG TCC TTG GAT TCC TTT CTC CTG AAT CAC AGC CTG GAG TAT        439
Lys Ser Leu Ser Leu Asp Ser Phe Leu Leu Asn His Ser Leu Glu Tyr
            120                 125                 130

ACA GTA GCT GCT CTT TCT TCT TGG TTA GAG TTC ACA CTT GAA AAT ATC        487
Thr Val Ala Ala Leu Ser Ser Trp Leu Glu Phe Thr Leu Glu Asn Ile
        135                 140                 145

TTT TGG CCA GAA CTG AAG CAG ATT ACC TGG CTC AGT GTC ACA GGG CTG        535
Phe Trp Pro Glu Leu Lys Gln Ile Thr Trp Leu Ser Val Thr Gly Leu
150                 155                 160

CTG ATG GTG GTC TTC GGA GAA TGT CTG AGG AAG GCG GCC ATG TTT ACA        583
Leu Met Val Val Phe Gly Glu Cys Leu Arg Lys Ala Ala Met Phe Thr
165                 170                 175                 180

GCT GGC TCC AAT TTC AAC CAC GTG GTA CAG AAT GAA AAA TCA GAT ACA        631
Ala Gly Ser Asn Phe Asn His Val Val Gln Asn Glu Lys Ser Asp Thr
                185                 190                 195

CAT ACT CTG GTG ACC AGT GGA GTG TAC GCT TGG TTT CGG CAT CCT TCT        679
His Thr Leu Val Thr Ser Gly Val Tyr Ala Trp Phe Arg His Pro Ser
            200                 205                 210

TAC GTC GGG TGG TTT TAC TGG AGT ATT GGA ACT CAG GTG ATG CTG TGT        727
Tyr Val Gly Trp Phe Tyr Trp Ser Ile Gly Thr Gln Val Met Leu Cys
        215                 220                 225

AAC CCC ATC TGC GGC GTC AGC TAT GCC CTG ACA GTG TGG CGA TTC TTC        775
Asn Pro Ile Cys Gly Val Ser Tyr Ala Leu Thr Val Trp Arg Phe Phe
230                 235                 240

CGC GAT CGA ACA GAA GAA GAA GAA ATC TCA CTA ATT CAC TTT TTT GGA        823
Arg Asp Arg Thr Glu Glu Glu Glu Ile Ser Leu Ile His Phe Phe Gly
245                 250                 255                 260

GAG GAG TAC CTG GAG TAT AAG AAG AGG GTG CCC ACG GGC CTG CCT TTC        871
Glu Glu Tyr Leu Glu Tyr Lys Lys Arg Val Pro Thr Gly Leu Pro Phe
                265                 270                 275

ATA AAG GGG GTC AAG GTG GAC CTG TGACGGGCAG TGGCCCCGGT GACCTTGGGG       925
Ile Lys Gly Val Lys Val Asp Leu
            280

CCTCCGACCC TGTGCAGCCT GGGACAAAAC TGTTTCCGGT TGGCCGCTGC CACATGGAT       985

TTCTTAATCG TTTTATGTCA TTAGTCACTC TTCTGGAATG TCACTCAAGA CCAAGCGG       1045

AGAAGGCCTG AGGACCCAAG GCCCCACTGG AGCAGTCTGT CCTTATGCCG AATCAAGG       1105

GAACATGGGT GAAAGACGAG TAAGGGGCAA ATCACAGCAA TATTCCACAG CGCCCTCC       1165

AGTTACCTGG GGAGGACCGA GGCCACACGC CACTGCCCCC GAGGCCAGAG TGTAAGTA       1225

GGATAACCAG GACTCGCTGG GAGAGATGGA CTCTGTCCTC AGCAACACTC CACAGCAG       1285

AGGGGTAGCA GGTACCCCTT CTTATCAGCG GTAAAAATGC ATTTACAACC TTTCATTT       1345

CCGAAAAACA CAGACCGCTT TAACCTCTTT ATTTCTGTCC CCCACTGCAT GAACATCT       1405
```

```
ACAATTTTAA AAATACTTCC TCATAGGATG CTTTGGCCCT TCATCTATTT AATCATAG      1465

ACATACCTAT TTTTTTATAA GTAGCAGTAC ACATTCAAAG GGGTATTCCT AGCTCAAT      1525

TTGGTGTTCT AGTTCAACTT TTATCCTGCA GCAAGTAAGC CTAGATAACT CTACACGA      1585

TGGCTGAGTG GCTTTGTGTG ACCGTGGCCC CAGGCCAAGG GGACCATGGC CCTGGCTG      1645

TTTCCCCCGG GGGTCTCAGC TCCTGTTGTC AGTGATAGGC GGCTCAAAGG AGCATCAG      1705

TCTTTTGATC CAAGAAGTGC TTACTGAATG CCTGCCCTGT GCGTGGCCTT AAACATTG      1765

AAGTGCTGCT CTCCGTTTAT TTGGGATTTG ATTCTCATTT TACCATAGCT TATATTCT      1825

ATTTCAATGC CAGTCTCAGA ACTCTTGTTT TCTGTGTTCT GTTCTCAAAA TTACATTG      1885

CCTCATGTCA TTTCAAACTG TTTTCCAAAG GGATTTGAGC ATATACAACT ACAAATCC      1945

GCAGATTGAC TCTCAAAAAT AATCTTAAAT ACTGCAAATA GTCCCAACTA AGATTCAG      2005

AGTATGTTTG TTTTGCAAGT TTGGGAGAGT AAGTTGGCTT TGAGTCACAC ATCGAAGC      2065

TAAGAGGTGA GACGCTGGCT TCATTCTGGA CTAGACAGGA ACTTGGCCTC AGCGTGAG      2125

CCTGCCATGC AGTGTTGCGG TGGCACTGAA GAAGTGTGAA TGTGAAGGCG GCGTCGGC      2185

GGGGCCAGAG CACCACTCTG CTGCCCCACC ACGCGGCCTG TGAGGAGCCA CTAAACCT      2245

CCGTGCCTAG ACCTCCCCAT CTGTGGAATG GGGTCAATAC CACCTACCTC ACAGGGGT      2305

TGTGAGGACT GAGAAGAACA ATGTCAAATG TTTTTAATAC TCAGATGTGG GAGCGACA      2365

AATGAAATCT GTACTGTATG AAAGCTACAC AAAAATGGGC AGACATTTGG TTAATTGT      2425

CAGATACCTA AAATGTATGT TCAGAAAAGC ATTTTATCAA CTCAGAAATA TGACTTAT      2485

CTAGATTCAT GGCTTAATGA ATTTTTTCAT TGTTATATAT ACCAAAGAGG CTTACGGG      2545

CATTGATTGG TTTGAAAACC AGACAGACGG CCGGGCACGC CTGTAATCCC AAAGTGCT      2605

GATTGCAGCG TGAGCCACCA CGCCCAGCCA AGATGAACTC CTTAAGGACA GGATTTGG      2665

AGTGATTGAC TTCTTTTTAG TTCCATGATC TTGAGATTAT TTTTAGCTTT ATAAATTT      2725

CAGTGGCAGG GCCCGTGGAG AATCAGGTTA ATGAGGTAAA GGCTTTCTGG GTATTTGC      2785

CCAAGGCCAC ATCACCAATT TTCTCGATTT AAAAAACTGT CAAGAGATTT ATTTTTCC      2845

TGCAGGTTTT AAAGTGGAGA TTCTGAAGTG GAAAATAGGT ACTGTCAGAA CAAAGCTA      2905

TGGAAACAGC ATAGAGTGAA GCCTTTCGTG AGGGCTTGCA GGCCGCTGCT GAGTGGCA      2965

TTACAGAAGA GGTCGCGGGG TGAGCCTCTT AGCAGGACAG AAAACAAGGC AGCAGCGC      3025

CTGCCACCCC TTCACGAGCT GCTCCTTGAG CCTAAAAAGT AGGCTTTATT CATCCCTT      3085

GTTCATTTAC CAACCTGGGG GATTGATACG ACCGGGGAAA ATGTTCCTAA ACCAGGAA      3145

TGCGTTAGCC GATCAGGCTT TGTAAGATCT CGCCAACAGC TAGCTGCTTA GGAGTACC      3205

CACGATACGC ACAGCACACC ACTGTCCCTT CACTGCACTT TCTTCCTGCC TTAGGTAG      3265

GGGCTTGCCC ACCCTAGTTT GCTTTTGTAG TGGTTTGGCA AGGTTAGAAG GCCTCGGC      3325

CTCTGTCATG CTGGGAAGTG CCTACTCTCT GGGCCACTGC TGCAGAGGCC GTGGCACT      3385

TCATGGGTTT GGAAGACCCA GCCATCTGCA GCAGAGGCAG CCTATCCCAT TGCAAGGA      3445

GGAACTGAAC GGAGTAATTA TTCTACTCTT CTTTTTACAT AAATGTTTAT TTAAATAT      3505

TAAATTGGAT TTTCATTCAC AGATACTGAT TATTCTTTCC AGTTCTTAAA TAAAACTG      3565

CTTGATTTCA CTCAAAAAAA AAAAAAAAA AA                                  3597
```

(2) INFORMATION FOR SEQ ID NO: 5:

(i) SEQUENCE CHARACTERISTICS:

(A) LENGTH: 284 amino acids
        (B) TYPE: amino acid
        (D) TOPOLOGY: linear (ii) MOLECULE TYPE: protein (xi) SEQUENCE DESCRIPTION: SEQ ID NO: 5:

Met Ala Gly Cys Ala Ala Arg Ala Pro Pro Gly Ser Glu Ala Arg Leu
 1               5                  10                  15

Ser Leu Ala Thr Phe Leu Leu Gly Ala Ser Val Leu Ala Leu Pro Leu
                20                  25                  30

Leu Thr Arg Ala Gly Leu Gln Gly Arg Thr Gly Leu Ala Leu Tyr Val
            35                  40                  45

Ala Gly Leu Asn Ala Leu Leu Leu Leu Tyr Arg Pro Pro Arg Tyr
 50                  55                  60

Gln Ile Ala Ile Arg Ala Cys Phe Leu Gly Phe Val Phe Gly Cys Gly
 65                  70                  75                  80

Thr Leu Leu Ser Phe Ser Gln Ser Ser Trp Ser His Phe Gly Trp Tyr
                85                  90                  95

Met Cys Ser Leu Ser Leu Phe His Tyr Ser Glu Tyr Leu Val Thr Ala
                100                 105                 110

Val Asn Asn Pro Lys Ser Leu Ser Leu Asp Ser Phe Leu Leu Asn His
        115                 120                 125

Ser Leu Glu Tyr Thr Val Ala Ala Leu Ser Ser Trp Leu Glu Phe Thr
130                 135                 140

Leu Glu Asn Ile Phe Trp Pro Glu Leu Lys Gln Ile Thr Trp Leu Ser
145                 150                 155                 160

Val Thr Gly Leu Leu Met Val Val Phe Gly Glu Cys Leu Arg Lys Ala
                165                 170                 175

Ala Met Phe Thr Ala Gly Ser Asn Phe Asn His Val Val Gln Asn Glu
                180                 185                 190

Lys Ser Asp Thr His Thr Leu Val Thr Ser Gly Val Tyr Ala Trp Phe
        195                 200                 205

Arg His Pro Ser Tyr Val Gly Trp Phe Tyr Trp Ser Ile Gly Thr Gln
        210                 215                 220

Val Met Leu Cys Asn Pro Ile Cys Gly Val Ser Tyr Ala Leu Thr Val
225                 230                 235                 240

Trp Arg Phe Phe Arg Asp Arg Thr Glu Glu Glu Ile Ser Leu Ile
                245                 250                 255

His Phe Phe Gly Glu Glu Tyr Leu Glu Tyr Lys Lys Arg Val Pro Thr
                260                 265                 270

Gly Leu Pro Phe Ile Lys Gly Val Lys Val Asp Leu
                275                 280

(2) INFORMATION FOR SEQ ID NO: 6:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

Cys Xaa Xaa Xaa
 1

```
(2) INFORMATION FOR SEQ ID NO: 7:

(i) SEQUENCE CHARACTERISTICS:
        (A) LENGTH: 173 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

Pro Gly Tyr Ser Arg Arg Phe Gly Pro Leu Val Arg Arg Leu Phe
1               5                   10                  15

Arg Arg Pro Ala His Gly Gly Cys Ala Ala Arg Phe Arg Gly Leu Arg
            20              25                  30

Gly Ala Pro Gln Pro Arg Tyr Ile Pro Pro Gly Arg Leu Gly Ala Arg
            35              40                  45

Ser Ala Ala Ala His Ala Arg Arg Pro Ala Gly Arg Thr Ala Leu Ala
            50              55                  60

Leu Tyr Val Ala Gly Leu Asn Ala Leu Leu Leu Leu Tyr Arg Pro
65              70                  75                  80

Pro Arg Tyr Gln Ile Ala Ile Arg Ala Cys Phe Leu Gly Phe Val Phe
                85              90                  95

Gly Cys Gly Val Leu Leu Ser Phe Ser Gln Ser Ser Trp Asn His Phe
            100             105                 110

Gly Trp Tyr Val Cys Ser Leu Ser Leu Phe His Tyr Glu Ser Tyr Leu
            115             120                 125

Val Thr Ala Val Asn Asn Pro Lys Ser Leu Ser Leu Asp Ser Phe Leu
            130             135                 140

Leu Asn His Ser Leu Glu Tyr Thr Val Ala Ala Leu Ser Ser Trp Ile
145             150                 155                 160

Glu Phe Thr Leu Glu Asn Ile Phe Trp Pro Glu Leu Lys
                165                 170

(2) INFORMATION FOR SEQ ID NO: 8:

(i) SEQUENCE CHARACTERISTICS:
        (A) LENGTH: 288 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

Met Ala Gly Ala Arg Leu Leu Gln Glu Gly Arg Val Ser Ile Val Ser
1               5                   10                  15

Phe Thr Leu Gly Ala Ser Val Ile Ser Leu Pro Leu Leu Thr Ser Ser
            20              25                  30

Phe Thr Glu Gln Thr Leu Leu Ala Ala Ala Pro Gly Arg Ile Ala Leu
            35              40                  45

Val Phe Phe Ile Ala Ala Leu Asn Gly Leu Leu Leu Leu Leu Tyr Lys
            50              55                  60

Ala Gln Leu Tyr Gln Val Ala Ile Arg Ala Ser Phe Leu Gly Phe Ala
65              70                  75                  80

Phe Gly Cys Gly Leu Leu Leu Ser Ile Thr Gln Ser Pro Trp Lys Pro
            85              90                  95

Phe Gly Trp Tyr Val Cys Ser Leu Ser Phe Phe His Tyr Ser Glu Tyr
            100             105                 110
```

```
Leu Val Thr Ala Met Asn Asn Pro Arg Ser Leu Ser Ile Asp Ser Phe
            115                 120                 125

Leu Leu Asn His Ser Leu Glu Tyr Thr Leu Ala Ala Leu Ser Ser Trr
            130                 135                 140

Val Glu Phe Thr Ile Glu Thr Thr Ile Tyr Pro Asp Leu Lys Gln Ile
145                 150                 155                 160

Thr Trp Leu Ser Val Ile Gly Leu Ile Met Val Leu Phe Gly Glu Val
                165                 170                 175

Leu Arg Lys Cys Ala Met Leu Thr Ala Gly Ser Asn Phe Asn His Ile
            180                 185                 190

Val Gln Asn Glu Lys Ser Asp Ser His Thr Leu Val Thr Ser Gly Val
            195                 200                 205

Tyr Ser Trp Phe Arg His Pro Ser Tyr Gly Val Trp Phe Tyr Trp Ser
            210                 215                 220

Ile Gly Thr Gln Val Leu Leu Cys Asn Pro Leu Cys Leu Val Gly Asp
225                 230                 235                 240

Thr Val Ala Ser Trp Arg Phe Phe Ser Glu Arg Ile Glu Glu Glu Glu
                245                 250                 255

Phe Ser Leu Ile His Phe Phe Gly Glu Asn Tyr Leu Glu Tyr Lys Lys
            260                 265                 270

Lys Val Pro Thr Gly Leu Pro Phe Ile Lys Gly Val Lys Met Glu Pro
            275                 280                 285

(2) INFORMATION FOR SEQ ID NO: 9:

(i) SEQUENCE CHARACTERISTICS:
        (A) LENGTH: 293 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

Met Pro Pro Ile Pro Pro Pro Thr Phe Val Gly Arg Ile Ala Phe His
1                   5                   10                  15

Leu Lys Ser Asp Asp Asp Phe Arg Thr Ala Ile Asp Ala Phe Met Ala
            20                  25                  30

Ser Phe Ala Val Val Ala Thr Val Ser Ala Ser Thr Ser Ser Phe Val
            35                  40                  45

Phe Gly Ile Leu Ala Ser Leu Leu Thr Ile Leu Ile Ala Tyr Leu Phe
    50                  55                  60

Ala Arg Lys Arg Val Phe Thr Asn Lys Ser Ile Leu Met Pro Ala Ala
65                  70                  75                  80

Leu Leu Gly Cys Ala Val Ala Val Ser Leu Ala Tyr Ser Val Ser His
            85                  90                  95

Glu Gly Glu Val Leu Glu His Leu Ser His Tyr Phe Leu Phe Leu Ser
            100                 105                 110

Met Phe His Phe Thr Glu Phe Val Phe Thr Ala Leu Thr Asn Arg Arg
            115                 120                 125

Thr Leu Arg Pro Asp Ser Phe Leu Leu Asn His Ser Val Gly Tyr Trp
            130                 135                 140

Leu Ala Ala Ser Ile Ser Trp Ile Glu Phe Leu Ile Glu Ala Tyr Phe
145                 150                 155                 160

Phe Pro Glu Ile Lys Met Arg Gly Ile Leu Trp Ile Gly Thr Leu Gly
            165                 170                 175
```

```
Cys Ile Ile Gly Glu Ile Phe Arg Lys Val Gly Met Val His Ala Gly
            180                 185                 190

Leu Ala Phe Thr His Arg Leu Ala Met Thr Lys Arg Ser Asp His Arg
            195                 200                 205

Leu Val Lys Asp Gly Ile Tyr Ala Tyr Leu Arg His Pro Gly Tyr Phe
            210                 215                 220

Gly Trp Phe Leu Trp Ala Val Ser Thr Gln Ile Ile Leu Cys Asn Pro
225                 230                 235                 240

Ile Cys Cys Val Val Tyr Ala Tyr Val Thr Trp His Phe Phe Ala Ser
                245                 250                 255

Arg Ile Tyr Asp Glu Glu Lys Asp Leu Ile Ser Phe Phe Gly Asp Ser
                260                 265                 270

Tyr Val Glu Tyr Gln Gln Asn Val Trp Cys Gly Val Pro Phe Val Arg
            275                 280                 285

Gly Tyr Gln Arg Pro
            290

(2) INFORMATION FOR SEQ ID NO: 10:

(i) SEQUENCE CHARACTERISTICS:
        (A) LENGTH: 295 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Met Ala Pro Asn Ser Thr Pro Pro Thr Phe Phe Gly Arg Ile Val
1               5                   10                  15

Phe His Leu Thr Ser Asp Asp Val Phe Arg Thr Ala Ile Phe Ala Phe
            20                  25                  30

Ile Ala Ser Phe Thr Val Ile Ala Val Ala Ser Val Thr Gly Ser
            35                  40                  45

Phe Leu Val Gly Leu Leu Ala Ser Val Ile Val Leu Val Ala Tyr
50                  55                  60

Ala Val Gly Glu Ser Cys Glu Phe Ile Asn Asn Gln Ile Leu Met Pro
65                  70                  75                  80

Ala Ala Phe Leu Gly Cys Ala Val Ala Val Asn Leu Val Tyr Thr Val
                85                  90                  95

Ala His Glu Gly Glu Leu Trp Glu Tyr Phe Ser Arg Tyr Phe Leu Phe
            100                 105                 110

Leu Ser Val Phe His Phe Ser Glu Phe Val Phe Thr Ala Leu Thr Asn
            115                 120                 125

Arg Arg Thr Leu Gly Pro Asp Ser Phe Leu Leu Lys His Ser Phe Gly
            130                 135                 140

Tyr Trp Leu Ala Ala Ser Ile Gly Trp Ile Glu Phe Leu Ile Glu Ala
145                 150                 155                 160

Asn Phe Tyr Pro Glu Ile Lys Met Tyr Ser Val Leu Trp Ile Gly Thr
                165                 170                 175

Phe Gly Cys Ile Ile Gly Glu Ile Phe Arg Lys Val Gly Met Val His
            180                 185                 190

Ala Gly Leu Ala Phe Thr His Leu Met Ala Arg Thr Lys Arg Ser Gly
            195                 200                 205

His Thr Leu Ile Asn Thr Gly Ile Tyr Ala Tyr Met Arg His Pro Gly
            210                 215                 220
```

-continued

```
Tyr Phe Gly Trp Phe Ile Trp Ala Val Ser Thr Gln Ile Val Leu Cys
225                 230                 235                 240

Asn Pro Ile Ser Phe Val Ile Tyr Thr Phe Val Thr Trp Arg Phe Phe
                245                 250                 255

Ala Asn Arg Ile Glu Ile Glu Glu Lys Asp Leu Ile Ser Phe Phe Gly
                260                 265                 270

Asp Asp Tyr Ala Glu Tyr Gln Arg Lys Thr Trp Ser Gly Val Pro Phe
            275                 280                 285

Ala Arg Gly Tyr Gln Lys Pro
            290             295
```

(2) INFORMATION FOR SEQ ID NO: 11:

(i) SEQUENCE CHARACTERISTICS:
        (A) LENGTH: 239 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

```
Met His Gln Asp Phe Gln Glu Asp Glu His Glu Tyr Pro Asp Ile Arg
1               5                   10                  15

Arg Asn Pro Leu His Glu Val Thr Met Thr Ser Tyr Ile Leu Gly Ile
                20                  25                  30

Leu Leu Gly Ile Phe Val Gly Leu Phe Pro Gln Ile Arg Phe Lys Asn
            35                  40                  45

Phe Asn Leu Phe Ile Ile Ala Leu Ser Leu Phe His Phe Leu Glu Tyr
50                  55                  60

Tyr Ile Thr Ala Lys Tyr Asn Pro Leu Lys Val His Ser Glu Ser Phe
65                  70                  75                  80

Leu Leu Asn Asn Gly Lys Ser Tyr Met Ala Ala His Ser Phe Ala Ile
                85                  90                  95

Leu Glu Cys Leu Val Glu Ser Phe Leu Phe Pro Asp Leu Lys Ile Phe
                100                 105                 110

Ser Tyr Ser Leu Ala Thr Lys Leu Cys Thr Val Leu Gly Cys Leu Leu
            115                 120                 125

Val Ile Leu Gly Gln Tyr Thr Arg Thr Ile Ala Met His Thr Ala Gly
130                 135                 140

His Ser Phe Ser Ile Val Lys Thr Lys Glu Ser Asp His Val
145                 150                 155                 160

Leu Val Lys Thr Gly Val Tyr Ser Trp Ser Arg His Pro Ser Tyr Leu
                165                 170                 175

Gly Phe Phe Trp Trp Ala Ile Gly Thr Gln Leu Leu Leu Leu Asn Pro
            180                 185                 190

Leu Ser Leu Val Ile Phe Ile Phe Val Leu Trp Lys Phe Ser Asp
            195                 200                 205

Arg Ile Arg Val Glu Glu Lys Tyr Leu Ile Glu Phe Phe Ser Ala Glu
210                 215                 220

Tyr Ile Glu Tyr Lys Asn Lys Val Gly Val Gly Ile Pro Phe Ile
225                 230                 235
```

(2) INFORMATION FOR SEQ ID NO: 12:

(i) SEQUENCE CHARACTERISTICS:
        (A) LENGTH: 236 amino acids
        (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO: 12:

Met Gly Asn Leu His Thr Ser Ile Ala Val Ala Ser Ile Cys Leu Thr
1               5                  10                 15

Ser Ala Phe Leu Gly Cys Val Phe Gly Leu Gly Phe Val Trp Ile
            20              25              30

Ile Tyr Gly Tyr Ser Ile Gly Gly Phe Phe Ala Phe Leu Ser Leu Phe
        35              40              45

His Phe Leu Glu Phe Tyr Ile Thr Ala Arg Phe Gln Gly Ser Gln Leu
    50              55              60

Ser Trp Asp Ser Phe Ile Leu Asn Asn Gly Lys Ala Tyr Trp Leu Ala
65              70              75              80

Met Leu Val Gly Leu Leu Glu Cys Leu Leu Ser Gly Gly Lys Ser Phe
            85              90              95

Ala Lys Val Ile Asn Cys Leu Arg Phe Pro Ser Phe Leu Ile Asn Phe
            100             105             110

Ile Phe Ser Val Tyr Gln Thr Ser Ala Leu Gly Phe Leu Cys Leu Gly
        115             120             125

Gln Tyr Leu Arg Ser Ser Ala Met Val Gln Ala Gly Gln Ser Phe Ser
    130             135             140

His Ile Val Ala Ser Lys Arg Asn Lys Asp His Leu Leu Val Thr Asp
145             150             155             160

Gly Ile Tyr Ala Tyr Val Arg His Pro Ser Tyr Val Gly Phe Phe Ile
            165             170             175

Trp Ala Leu Gly Thr Gln Met Leu Leu Gly Asn Phe Val Ser Thr Leu
            180             185             190

Leu Phe Ser Leu Val Leu Trp Lys Phe Phe Ser Gln Arg Ile Thr Thr
        195             200             205

Glu Glu Ala Tyr Leu Val Ser Phe Phe Gly Asp Ser Tyr Glu Gln Tyr
    210             215             220

Arg Lys Lys Val Pro Ser Gly Ile Pro Leu Ile Pro
225             230             235

(2) INFORMATION FOR SEQ ID NO: 13:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Gly Gly Tyr Gln Lys Arg Ala Cys
1               5
```